(12) United States Patent
Bergman et al.

(10) Patent No.: US 11,338,072 B2
(45) Date of Patent: May 24, 2022

(54) BLOOD TREATMENT SYSTEMS AND RELATED COMPONENTS AND METHODS

(71) Applicant: Fresenius Medical Care Holdings, Inc., Waltham, MA (US)

(72) Inventors: Eric Bergman, Newton, MA (US); Lynn E. Jensen, Syracuse, UT (US)

(73) Assignee: Fresenius Medical Care Holdings, Inc., Waltham, MA (US)

(*) Notice: Subject to any disclaimer, the term of this patent is extended or adjusted under 35 U.S.C. 154(b) by 30 days.

(21) Appl. No.: 16/848,410

(22) Filed: Apr. 14, 2020

(65) Prior Publication Data

US 2021/0316051 A1   Oct. 14, 2021

(51) Int. Cl.
*A61M 1/16* (2006.01)
*A61M 1/26* (2006.01)
(Continued)

(52) U.S. Cl.
CPC .......... *A61M 1/1603* (2014.02); *A61M 1/262* (2014.02); *A61M 1/3656* (2014.02); *B01D 61/30* (2013.01); *B01D 61/32* (2013.01); *A61M 2205/3306* (2013.01); *A61M 2205/3327* (2013.01)

(58) Field of Classification Search
CPC .. A61M 1/1603; A61M 1/262; A61M 1/3656; A61M 2205/3327; A61M 2205/3306; A61M 1/1601; A61M 1/3653; A61M 2205/332; A61M 2210/083; B01D 61/24; B01D 61/30; B01D 61/32; A61B 5/00; A61B 5/11; A61B 5/1126;
(Continued)

(56) References Cited

U.S. PATENT DOCUMENTS 5,895,571 A * 4/1999 Utterberg ................ A61M 1/16
210/241
6,806,947 B1 * 10/2004 Ekdahl ................ A61M 1/3626
356/339
(Continued)

FOREIGN PATENT DOCUMENTS

| DE | 102018106226 | 9/2019 |
| JP | 2016-214293 | 12/2016 |
| WO | 2019/207082 | 10/2019 |

OTHER PUBLICATIONS

Tsetserukou et al., "Safe Reaction of a Robot Arm with Torque Sensing Ability on the External Disturbance and Impact: Implementation of a New Variable Impedance Control," Proc. 16th International Symposium on Measurement and Control in Robotics (ISMCR 2007), Warsaw, Poland, Jun. 21-23, 2007, 10 pages.
(Continued)

*Primary Examiner* — Joseph W Drodge
(74) *Attorney, Agent, or Firm* — Fish & Richardson P.C.

(57) ABSTRACT

This disclosure relates to a blood treatment system including a blood treatment machine, a dialyzer configured to be coupled to the blood treatment machine, a blood line having a first end configured to be connected to the dialyzer and a second end configured to be connected to a needle for insertion into a patient, and one or more sensors operable to transmit, to the blood treatment machine, data related to tension along the blood line. The blood treatment machine is configured to take action in response to the data received from the one or more sensors.

27 Claims, 9 Drawing Sheets

(51) Int. Cl.
*A61M 1/36* (2006.01)
*B01D 61/30* (2006.01)
*B01D 61/32* (2006.01)

(58) Field of Classification Search
CPC ... A61B 5/1128; A61B 5/6824; A61B 5/1535; A61B 5/489
See application file for complete search history.

(56) References Cited

U.S. PATENT DOCUMENTS

| | | | |
|---|---|---|---|
| 9,731,068 B2* | 8/2017 | Rochette | A61M 5/14566 |
| 2005/0038325 A1* | 2/2005 | Moll | A61M 1/3656 |
| | | | 600/300 |
| 2009/0082649 A1* | 3/2009 | Muller | A61M 1/3659 |
| | | | 600/310 |
| 2012/0123322 A1* | 5/2012 | Scarpaci | A61M 1/3656 |
| | | | 604/29 |
| 2012/0160033 A1* | 6/2012 | Kow | A61M 5/5086 |
| | | | 73/861.71 |
| 2012/0234099 A1* | 9/2012 | Rochette | A61M 5/14566 |
| | | | 73/756 |
| 2013/0245531 A1* | 9/2013 | Brandl | A61M 39/105 |
| | | | 604/4.01 |
| 2014/0298891 A1* | 10/2014 | Holmer | A61M 1/3656 |
| | | | 73/37 |
| 2015/0164437 A1* | 6/2015 | McCombie | A61B 5/1114 |
| | | | 600/301 |
| 2016/0310077 A1* | 10/2016 | Hunter | A61F 2/16 |
| 2017/0119258 A1* | 5/2017 | Kotanko | A61M 1/3656 |
| 2019/0117873 A1* | 4/2019 | Lazar | A61M 1/3655 |
| 2019/0255244 A1* | 8/2019 | Lazar | A61M 1/14 |
| 2019/0380645 A1* | 12/2019 | Kopperschmidt | A61B 8/0891 |
| 2020/0405942 A1 | 12/2020 | Hauke et al. | |
| 2021/0138135 A1 | 5/2021 | Fini et al. | |
| 2021/0187183 A1 | 6/2021 | Czerwonka | |
| 2021/0236025 A1* | 8/2021 | Comtois | A61B 5/1121 |

OTHER PUBLICATIONS

PCT International Search Report and Written Opinion in International Appln No. PCT/US2021/026507, dated Jul. 8, 2021, 13 pages.

* cited by examiner

BLOOD TREATMENT SYSTEMS AND RELATED COMPONENTS AND METHODS

TECHNICAL FIELD

This disclosure relates to blood treatment systems and related components and methods.

BACKGROUND

Hemodialysis is a treatment used to support a patient with insufficient renal function. During hemodialysis, a patient's blood is passed through a dialyzer of a dialysis machine while also passing a dialysis solution or dialysate through the dialyzer. Dialyzers include a housing and a semi-permeable membrane contained within the housing of the dialyzer. The semi-permeable membrane separates the blood from the dialysate within the dialyzer and allows diffusion and osmosis exchanges to take place between the dialysate and the blood stream. An arterial blood line is typically connected at one end to the dialyzer and at the opposite end to a patient to carry the blood from the patient to the dialyzer during hemodialysis. A venous blood line is typically connected at one end to the dialyzer and at the opposite end to the patient to carry the filtered blood from the dialyzer back to the patient during hemodialysis.

SUMMARY

In one aspect, a blood treatment system includes a blood treatment machine, a dialyzer configured to be coupled to the blood treatment machine, a blood line having a first end configured to be connected to the dialyzer and a second end configured to be connected to a needle for insertion into a patient, and one or more sensors operable to transmit, to the blood treatment machine, data related to tension along the blood line. The blood treatment machine is configured to take action in response to the data received from the one or more sensors.

Embodiments can include one or more of the following features in any combination.

In certain embodiments, the blood treatment machine includes a treatment module including a structure for coupling with the dialyzer, a blood treatment machine console configured to control the treatment module, and an arm coupled to and extending between the treatment module and the blood treatment machine console. The blood treatment machine console is configured to control movement of the arm to automatically reposition the treatment module in response to the data received from the one or more sensors In some embodiments, the arm is configured to move the treatment module in a direction determined, based on the data related to tension along the blood line, to prevent disconnection of the blood line from the dialyzer or dislodgement of the needle from the patient.

In certain embodiments, the one or more sensors are configured to wirelessly transmit the data related to tension along the blood line to the blood treatment machine console.

In some embodiments, the arm includes one or more adjustable joints by which the arm can be articulated into multiple differing positions relative to the blood treatment machine console. In certain embodiments, the arm is configured to be manually articulated into multiple differing positions relative to the blood treatment machine console.

In some embodiments, the one or more sensors are configured to detect strain along the blood line.

In certain embodiments, the one or more sensors are attached to a treatment module of the blood treatment machine, and each of the one or more sensors is in contact with the blood line.

In some embodiments, at least one of the one or more sensors is coupled to the treatment module.

In certain embodiments, at least one of the one or more sensors is positioned along the blood line proximate a patient end of the blood line.

In some embodiments, the one or more sensors are embedded within the blood line.

In certain embodiments, at least one of the one or more sensors is coupled to a joint of an arm that extends from and is coupled to a treatment module of the blood treatment machine.

In some embodiments, the one or more sensors are configured to detect a position of a portion of the blood line.

In certain embodiments, the one or more sensors include one or more accelerometers coupled to the blood line.

In some embodiments, the one or more sensors include one or more image sensors configured to detect the position of the portion of the blood line.

In certain embodiments, the one or more sensors are configured to detect a position of a patient connected to the blood line.

In some embodiments, the one or more sensors include an image sensor configured to detect light reflected by a reflective material.

In certain embodiments, the blood treatment system further includes a device that includes the reflective material, the device being configured to be positioned on an arm of the patient proximate the blood line.

In some embodiments, the one or more sensors include an image sensor configured to track movement of an arm of the patient.

In another aspect, a blood treatment machine includes a treatment module including a structure for coupling with a dialyzer, a blood treatment machine console configured to control the treatment module, and an arm coupled to and extending between the treatment module and the blood treatment machine console. The blood treatment machine console is configured to control movement of the arm to automatically reposition the treatment module in response to data received from one or more sensors related to tension along a blood line coupled to the dialyzer.

Embodiments can include one or more of the following features in any combination.

In some embodiments, the arm includes one or more adjustable joints by which the arm can be articulated into multiple differing positions relative to the blood treatment machine console.

In certain embodiments, the arm is configured to be manually articulated into multiple differing positions relative to the blood treatment machine console In some embodiments, the data received from one or more sensors includes data related to tension along a blood line coupled to the dialyzer and to a needle inserted in a patient.

In certain embodiments, the arm is configured to move the treatment module in a direction determined, based on the data related to tension along the blood line, to prevent disconnection of the blood line from the dialyzer or dislodgement of the needle from the patient.

In some embodiments, the data received from the one or more sensors includes data related to strain along the blood line.

In certain embodiments, the data received from the one or more sensors includes data related to a position of a portion of a blood line coupled to the dialyzer.

In some embodiments, the data received from the one or more sensors includes image data related to the position of the portion of the blood line.

In certain embodiments, the data received from one or more sensors includes data related to a position of a patient connected to a blood line coupled to the dialyzer.

In some embodiments, the data received from the one or more sensors includes image data indicating light reflected by a reflective material.

In certain embodiments, the data received from the one or more sensors includes image data indicating a position of the arm of the patient.

In another aspect, a device includes one or more sensors configured to detect and transmit data related to tension along a blood line coupled to a dialyzer.

Embodiments can include one or more of the following features in any combination.

In some embodiments, the one or more sensors are configured to detect strain along the blood line.

In certain embodiments, each of the one or more sensors is in contact with the blood line.

In some embodiments, at least one of the one or more sensors is positioned to contact a portion of the blood line proximate a patient end of the blood line.

In certain embodiments, at least one of the one or more sensors is coupled to a treatment module coupled to the dialyzer.

In some embodiments, the one or more sensors are embedded within the blood line.

In certain embodiments, the one or more sensors are configured to detect strain along the blood line in three dimensions.

In some embodiments, the one or more sensors are configured to detect a three dimensional position of a portion of the blood line.

In certain embodiments, the one or more sensors include one or more accelerometers coupled to the blood line.

In some embodiments, the one or more sensors are configured to detect a position of a patient connected to the blood line.

In certain embodiments, the one or more sensors include an image sensor configured to detect light reflected by a reflective material positioned on an arm of the patient proximate the blood line.

In some embodiments, the one or more sensors include an accelerometer coupled to an arm of the patient.

In certain embodiments, the one or more sensors transmit signals indicating the position of the arm of the patient using near field communication.

In some embodiments, the one or more sensors include an image sensor configured to track movement of an arm of the patient.

In another aspect, a method includes receiving a signal from one or more sensors indicating a status of a blood line that has a first end connected to a dialyzer and a second end connected to a needle inserted in a patient; and moving a blood treatment module coupled to the dialyzer based on the signal to prevent disconnection of the blood line from the dialyzer or dislodgement of the needle from the patient.

Embodiments can include one or more of the following features in any combination.

In certain embodiments, moving the blood treatment module includes controlling a robotic arm coupled to the blood treatment module to reposition the blood treatment module.

In some embodiments, moving the blood treatment module includes extending the robotic arm towards the patient to generate slack in the blood line.

In certain embodiments, moving the blood treatment module includes moving the blood treatment module in a direction that reduces tension in the blood line.

In some embodiments, moving the blood treatment module includes moving the blood treatment module in three dimensions.

In certain embodiments, moving the blood treatment module includes moving the blood treatment module at a speed determined based on the signal indicating the status of the blood line.

In some embodiments, the signal indicates strain along the blood line.

In certain embodiments, the method further includes following receiving the signal indicating strain along the blood line and before moving the blood treatment module, receiving a second signal indicating a decreased strain in the blood line; and in response to receiving the second signal, controlling a blood pump fluidly coupled to the blood line to cease pumping.

In some embodiments, the method further includes in response to receiving the second signal, transmitting an alert indicating disconnection of the blood line or dislodgement of the needle.

In certain embodiments, the method further includes after moving the blood treatment module, receiving a second signal indicating a change in strain in the blood line below a threshold amount; and in response to receiving the second signal, transmitting an alert indicating a snag in the blood line.

In some embodiments, the signal indicates a strain in the blood line above a threshold strain.

In certain embodiments, the signal indicates a position of an arm of the patient connected to the blood line.

In some embodiments, moving the blood treatment module includes moving the blood treatment module towards the detected position of the arm of the patient In certain embodiments, wherein the signal indicates a position of a patient end of the blood line.

In some embodiments, moving the blood treatment module includes moving the blood treatment module towards the detected position of the patient end of the blood line.

In certain embodiments, the method further includes receiving a signal indicating completion of a dialysis treatment; and in response to receiving the signal indicating completion of the dialysis treatment, moving the blood treatment module to a predetermined position.

Advantages of the systems, devices, and methods described herein can include reduced risk of disconnection of blood lines from a dialyzer of a blood treatment machine during hemodialysis treatment. In addition, the systems, devices, and methods described herein can reduce the risk of dislodgement of needles connected to the blood lines from the patient during treatment. For example, by using sensors to detect strain within one or more of the blood lines attached to a patient and to a dialyzer during hemodialysis treatment, the position of a treatment module coupled to the dialyzer can be dynamically adjusted to reduce tension along the blood lines, which reduces the risk of disconnection of the blood lines from the dialyzer and/or dislodgement of needles from the patient. In addition, by using a system of sensors to detect strain in the blood lines and a robotic arm operable to dynamically adjust the position of the treatment module in response to detected strain, the blood lines can be quite short compared to blood lines used in conventional blood treatment systems. This reduction in blood line length reduces the cost of the blood lines, as well as reduces the volume of blood outside the body of the patient, which provides for improved control of patient blood pressure and reduced risk of complications related to reduced blood volume. In addition, by enabling the use of shorter blood lines, the systems and methods described herein reduce the risk of snags along the blood lines, which further reduces the risk of dislodgement of needles from the patient or disconnection of the blood lines from the dialyzer.

Other aspects, features, and advantages of the invention will be apparent from the description and drawings, and from the claims.

DETAILED DESCRIPTION

Figure 1:
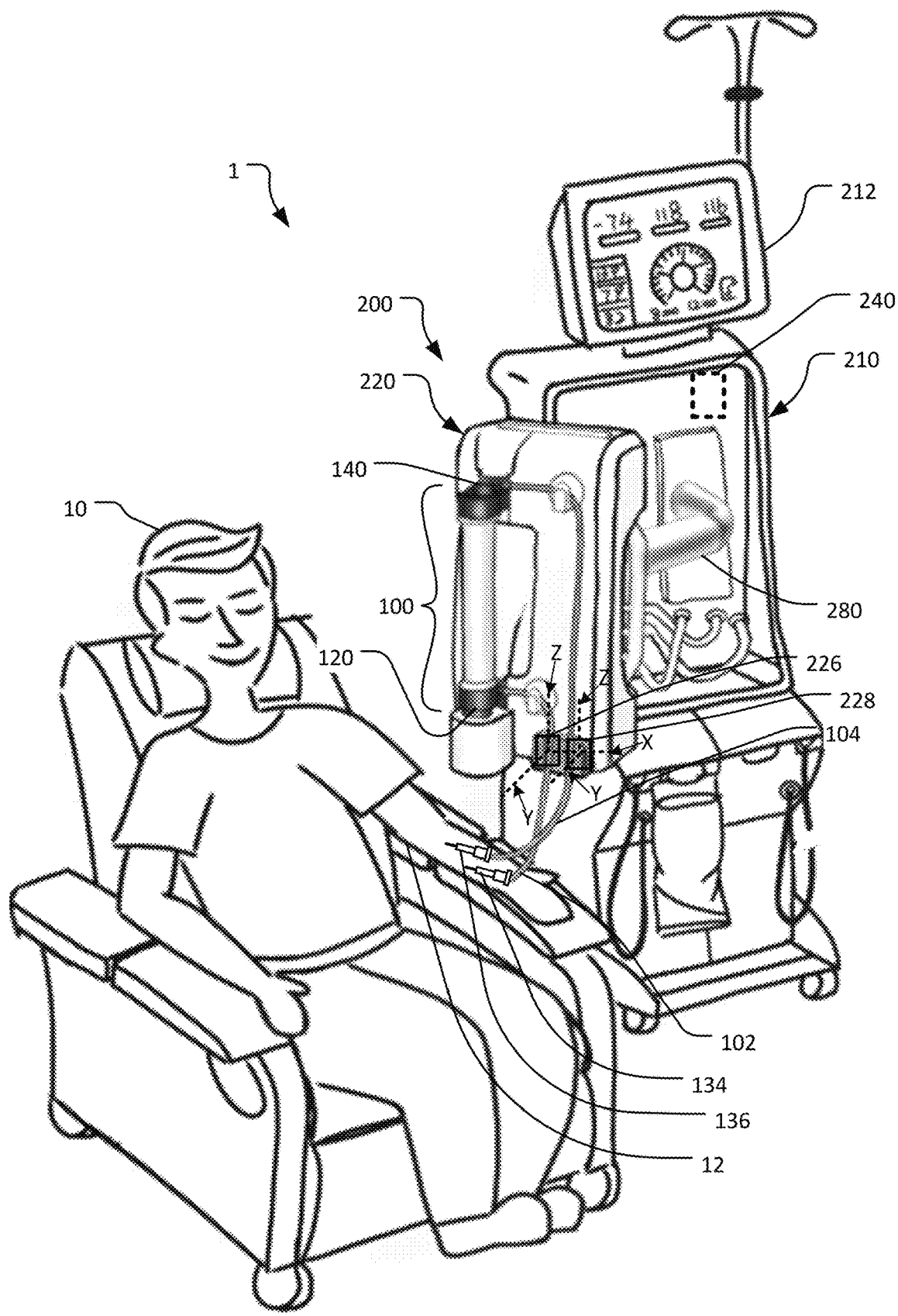
FIG. 1 depicts a patient receiving an extracorporeal blood treatment using a blood treatment system.

With reference to FIG. 1, a patient 10 is depicted as receiving an extracorporeal blood treatment using a blood treatment system 1 that includes a disposable set connected to a blood treatment machine 200. The disposable set includes a dialyzer 100 that is coupled to a treatment module 220 of the blood treatment machine 200. The system 1 can be used to provide one or more types of treatment to the patient 10, including hemodialysis (HD), hemodiafiltration (HDF), or some other type of blood treatment. For such treatments, blood is withdrawn from the patient 10 via an arterial line 102 and, after passing through the dialyzer 100, treated blood is returned to the patient 10 via a venous line 104. The patient 10 is connected to the arterial line 102 and venous line 104 using needles 134 and 136, respectively. The dialyzer 100, arterial line 102, venous line 104, and needles 134, 136 are single-use disposable items, whereas the blood treatment machine 200 is a durable reusable system. In some cases, a single dialyzer 100 may be reused two or more times for a particular individual patient.

In addition to the treatment module 220, the blood treatment machine 200 includes a blood treatment machine console 210 and an arm 280 that connects the treatment module 220 to the blood treatment machine console 210. The blood treatment machine 200 can be used in both outpatient treatment centers and home settings. The blood treatment machine console 210 includes a user interface 212, a control system, facilities for making dialysate, and the like.

A first end of the arm 280 of the blood treatment machine 200 is coupled to and extends from the blood treatment machine console 210 and a second end of the arm 280 is coupled to the treatment module 220. As such, the treatment module 220 is cantilevered from the blood treatment machine console 210 by the arm 280. The arm 280 is coupled to the blood treatment machine console 210 and the treatment module 220 using any suitable mechanical fasteners, including, but not limited to, screws and bolts.

The arm 280 includes one or more adjustable joints that enable the arm 280 to be manually articulated to position the treatment module 220 in various positions/orientations relative to the blood treatment machine console 210 and/or relative to the patient 10. For example (as depicted in FIG. 1), the arm 280 can be extended so that the treatment module 220 is positioned close to the patient 10. In some cases the adjustable joints of the arm 280 enable three dimensional movement such that the arm 280 can be extended and retracted, as well as move the treatment module 220 up and down and side to side. As such, the arm 280 is fully articulated with three degrees of freedom. Accordingly, the arterial line 102 and the venous line 104 (also referred to as blood lines 102, 104) can be quite short as compared to blood lines used with most conventional blood treatment systems. For example, in some embodiments, the arterial line 102 and the venous line 104 have a length less than one meter (e.g., less than 90 cm, less than 80 cm, less than 70 cm, less than 60 cm, less than 50 cm, less than 40 cm, less than 30 cm, or less than 20 cm).

In some implementations, the arm 280 is configured to allow the treatment module 220 to be tilted upwards or downwards on the end of the arm 280. For example, the treatment module 220 may be tilted about the end of the arm 280 to allow an operator of the blood treatment machine 200 to have improved access to the treatment module 220.

As depicted in FIG. 1, the blood treatment system 1 also includes an arterial line sensor 226 and a venous line sensor 228. The sensors 226, 228 are each positioned on and electrically coupled to the treatment module 220. As shown in FIG. 1, the arterial line sensor 226 is coupled to the treatment module 220 and positioned on the treatment module 220 such that when the arterial line 102 is connected to the dialyzer 100, the arterial line sensor 226 is in physical contact with the arterial line 102. Similarly, the venous line sensor 228 is coupled to the treatment module 220 and is positioned on the treatment module 220 such that when the venous line 104 is connected to the dialyzer 100, the venous line sensor 228 is in physical contact with the venous line 104.

The arterial line sensor 226 and venous line sensor 228 are each configured to detect tension along a respective blood line 102, 104. For example, the arterial line sensor 226 detects strain along the arterial line 102 when the arterial line 102 is in contact with the arterial line sensor 226 while the venous line sensor 228 detects strain along the venous line 104 when the venous line 104 is in contact with the venous line sensor 228. The sensors 226, 228 can include any suitable type of sensor for detecting strain including, but not limited to, strain gauges, resistors, load cells, etc.

The strain detected by the sensors 226, 228 along the arterial line 102 and the venous line 104 can be transmitted by the sensors 226, 228 to the blood treatment machine console 210. For example, the sensors 226, 228 can be electrically wired to the treatment module 220 to communicate signals indicating the detected strain to the treatment module 220, and the treatment module 220 can be electrically wired to, or otherwise communicably coupled with, the blood treatment machine console 210 and can transmit the signal received from the sensors 226, 228 to the blood treatment machine console 210. In some implementations, the sensors 226, 228 are electrically wired directly to the blood treatment machine console 210 to communicate signals indicating the detected strain to the blood treatment machine console 210. In some implementations, for example, the sensors 226, 228 are wireless sensors configured to wirelessly communicate signals indicating the detected strain to the blood treatment machine console 210 (e.g., via Bluetooth or WiFi). As will be described in further detail herein, the blood treatment machine console 210 can control the arm 280 to reposition the treatment module 220 in a position that reduces the strain detected along blood lines 102, 104 detected by the sensors 226, 228.

Figure 2:
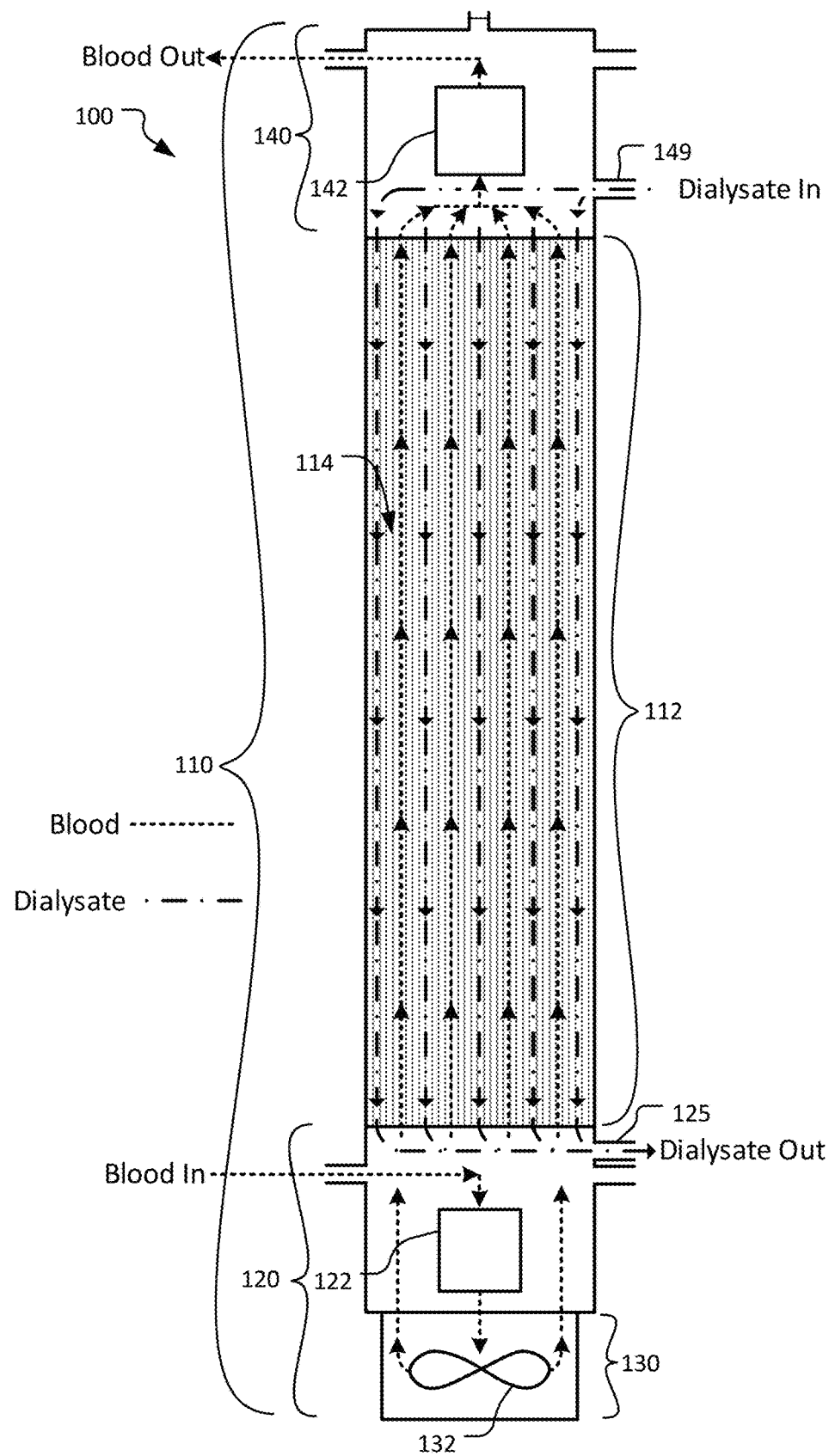
FIG. 2 is a schematic depiction of the dialyzer of the blood treatment system of FIG. 1.

FIG. 2 is a schematic diagram of the dialyzer 100. As depicted in FIG. 2, the housing 110 of the dialyzer 100 includes a first end cap 120, a second end cap 140, and a middle housing portion 112 that extends between the first end cap 120 and the second end cap 140. The middle housing portion 112 contains the majority of the length of a bundle of hollow fibers 114. As depicted in FIG. 1, the arterial line 102 is connected to the first end cap 120 of the dialyzer 100 and the venous line 104 is connected to the second end cap 140 of the dialyzer 100.

Still referring to FIG. 2, the first end cap 120 includes a pump housing 130. A rotatable centrifugal pump rotor 132 is enclosed or encased within the pump housing 130. Accordingly, the pump rotor 132 is contained at a fixed position relative to the bundle of hollow fibers 114. The pump rotor 132 is operated and controlled by interfacing with a controller 240 of the blood treatment machine 200. That is, the pump rotor 132 can be levitated and rotated by magnetic fields that are caused to emanate from the pump drive unit during use. The depicted embodiment includes an arterial pressure detection chamber 122 and a venous pressure detection chamber 142. The pressure detection chambers 122 and 142 are each configured to interface with a respective pressure transducer of the treatment module 220.

The dialyzer 100 is configured to receive blood from the patient 10, and to direct the blood to flow through the housing 110 of the dialyzer 100. For example, blood flows into the first end cap 120 via the arterial line 102 (shown in FIG. 1). The fluid flow path entering the first end cap 120 is transverse to a longitudinal axis of the dialyzer 100. The blood flow path transitions to parallel to the longitudinal axis of the dialyzer 100 to deliver the blood to the pump rotor 132. The blood is directed to a center of the pump rotor 132. Rotations of the centrifugal pump rotor 132 force the blood radially outward from the pump rotor 132. Then, after flowing radially outward from the pump rotor 132, the blood turns and flows longitudinally toward the middle housing portion 112. The blood enters the lumens of the bundle of hollow fibers 114 and continues flowing longitudinally toward the second end cap 140. After passing through the middle housing portion 112, the blood exits the bundle of hollow fibers 114, enters the second end cap 140, and flows transversely out of the second end cap 140 via the venous line 104.

The dialyzer 100 is also configured to receive dialysate, and to direct the dialysate to flow through the housing 110. For example, in the depicted embodiment, the second end cap 140 defines a dialysate inlet port 149 and the first end cap 120 defines a dialysate outlet port 125. The dialysate flows into the second end cap 140 via the dialysate inlet port 149, and then enters the middle housing portion 112 containing the bundle of hollow fibers 114. The dialysate flows through the middle housing portion 112 via the spaces defined between the outer diameters of the fibers of the bundle of hollow fibers 114. While the blood flows within the lumens of the fibers of the bundle of hollow fibers 114, the dialysate liquid flows along the outsides of the fibers. The semi-permeable walls of the fibers of the bundle of hollow fibers 114 separate the dialysate liquid from the blood. The dialysate liquid flows out of the middle housing portion 112 and into the first end cap 120. The dialysate liquid exits the first end cap 120 via the dialysate outlet port 125. The dialyzer 100 depicted in FIG. 2 and certain other features of the blood treatment system 1 are described in further detail in U.S. Provisional Patent Application No. 62/934,228, filed on Nov. 12, 2019 and entitled "Blood Treatment Systems," which is incorporated herein by reference in its entirety.

Referring to FIGS. 1 and 2, a method of performing hemodialysis using the blood treatment system 1 will now be described.

Before hemodialysis treatment is initiated, the dialyzer 100 is attached to the control module 220 and one end of each of the blood lines 102, 104 is attached to the dialyzer 100. The opposite ends of the blood lines 102, 104 are attached to the patient 10 using needles 134, 136. Once the dialyzer 100 is connected to the treatment module 220 and the blood lines 102, 104 are attached to both the dialyzer 100 and the patient 10 (via connection to needles 134, 136), hemodialysis treatment can be initiated. The patient 10 or another operator of the blood treatment machine 200 can, for example, use a user interface 212 of the blood treatment machine console 210 to initiate the hemodialysis treatment.

During hemodialysis treatment, the pump rotor 132 of the dialyzer is driven such that blood in the arterial line 102 is drawn from the patient 10, directed through the dialyzer 100, and through the venous line 104 back into the patient 10. For example, upon initiating the hemodialysis treatment, blood flows from the patient 10 through the arterial line 102, into the first end cap 120 of the dialyzer 100, and through an arterial pressure detection chamber 122 towards the pump rotor 132 in the pump housing 130. As previously discussed, the pump rotor 132 is operated and controlled by interfacing with a pump drive unit of the treatment module 220. The rotation of the pump rotor 132 generates increased pressure within the dialyzer 100, which causes the blood within the dialyzer 100 to be pushed through the interior spaces (or lumens) of each of the hollow fibers of the bundle of hollow fibers 114.

As blood flows through the dialyzer 100, dialysate flows from the second end cap 140 of the dialyzer 100 to the first end cap 120 of the dialyzer 100 along the outer surfaces of the hollow fibers 114, such as within the spaces defined between the hollow fibers 114. Dialysis takes place across the semipermeable fiber membranes with the dialysate flowing (in a counterflow direction) in the space surrounding the fibers 114, with waste substances from the blood diffusing across the semipermeable fiber membranes of the hollow fibers 114 into the dialysate. The blood then flows, still within the hollow fibers 114, through a venous pressure detection chamber 142 in the second end cap 140. The blood exits the dialyzer 100 via the venous line 104, which conveys the dialyzed or filtered blood back to the patient 10. The spent dialysate flows to the first end cap 120 and exits the dialyzer 100 via a spent dialysate tube into a spent dialysate conduit of the treatment module 220. This hemodialysis process is continued until the treatment is complete.

Throughout the hemodialysis treatment, sensors 226, 228 monitor tension along the blood lines 102, 104, respectively, and transmit signals in real-time to the blood treatment machine console 210 indicating detected tension along the blood lines 102, 104. For example, during hemodialysis treatment, sensors 226, 228 monitor the amount of strain along the blood lines 102, 104, respectively, and transmit signals in real-time to the blood treatment machine console 210 indicating the amount of strain detected along the blood lines 102, 104. For example, if a patient 10 receiving the hemodialysis treatment moves his or her arm 12 away from the treatment module 220, the strain along the arterial line 102 and along the venous line 104 attached to the patient may increase as a result of the movement. In addition, if the arterial line 102 or the venous line 104 snag or catch on surrounding objects, strain in the arterial line 102 and the venous line 104 may increase. To detect these increases in strain along the blood lines 102, 104, the sensors 226, 228 continuously monitor the strain along the blood lines 102, 104 throughout the hemodialysis treatment and transmit signals indicating the strain along the respective blood lines 102, 104 in real-time to the blood treatment machine console 210.

The signals transmitted by the sensors 226, 228 to the blood treatment machine console 210 can indicate both the magnitude and the direction of the strain detected along the blood lines 102, 104. For example, the arterial line sensor 226 is configured to detect strain along the X axis, Y axis, and Z axis of the arterial line 102, and can transmit the $\varepsilon_x$, $\varepsilon_y$, and $\varepsilon_z$ strain components to the blood treatment machine console 210, which indicate the amount of strain experienced by the arterial line 102 along each of the axes. Similarly, the venous line sensor 228 is configured to detect strain along the X axis, Y axis, and Z axis of the venous line 104, and transmits the $\varepsilon_x$, $\varepsilon_y$, and $\varepsilon_z$ strain components to the blood treatment machine console 210, which indicate the amount of strain experienced by the venous line 104 along each of the axes.

Based on the signals received from one or more of the sensors 226, 228, the blood treatment machine console 210 moves the treatment module 220 to prevent disconnection of the blood lines 102, 104 from the dialyzer 100 or dislodgement of the needles 134, 136 from the patient 10. For example, in response to detecting increased strain along the blood lines 102, 104 based on the signals received from the sensors 226, 228, the blood treatment machine console 210 controls the arm 280 to reposition the module 220 to relieve the strain in the blood lines 102, 104. For example, based on the magnitude and direction of the strain along the arterial line 102 detected by the arterial line sensor 226, a control unit 240 of the blood treatment machine 200 determines the direction and distance the treatment module 220 must be moved in order to reduce the strain along the arterial line 102 by an amount sufficient to prevent disconnection of the arterial line 102 from the dialyzer 100 or dislodgement of needle 134 from the patient 10. Similarly, based on the magnitude and direction of the strain detected along the venous line 104 by the venous line sensor 228, the control unit 240 of the blood treatment machine console 210 determines the direction and distance the treatment module 220 must be moved in order to reduce the strain along the venous line 104 by an amount sufficient to prevent disconnection of the venous line 104 from the dialyzer 100 or dislodgement of needle 136 from the patient 10.

In some implementations, the control module of the blood treatment machine console 210 determines whether strain along one or more of the blood lines 102, 104 as detected by the sensors 226, 228 exceeds a threshold strain. In response to determining that the strain along one or more of the blood lines 102, 104, as detected by the sensors 226, 228, exceeds a threshold strain, the blood treatment machine console 210 can determine the direction and distance the treatment module 220 must be moved to reduce the strain along the blood(s) lines 102, 104 by an amount sufficient to prevent disconnection of the blood lines 102, 104 from the dialyzer 100 or dislodgement of the needles 134, 136 from the patient 10.

In some implementations, after receiving the first signal from the sensor(s) 226, 228 indicating strain along one or more of the blood lines 102, 104, and before moving the arm 280 to relieve the detected strain, the blood treatment machine console 210 receives a second signal from the respective sensor(s) 226, 228 indicating an updated strain measurement along the respective blood line(s) 102, 104. In response to receiving the second signal from the sensor(s) 226, 228, the blood treatment machine console 210 determines whether further action is required.

For example, in some implementations, if the first signal received by the blood treatment machine console 210 from the arterial line sensor 226 indicates strain along the arterial line 102, and the second signal received from the arterial line sensor 226 prior to movement of arm 280 indicates that the strain along the arterial line 102 has increased, the blood treatment machine console 210 will determine whether the strain along the arterial line 102 has increased more than a threshold amount. In response to detecting that the strain along the arterial line 102 has increased more than a threshold amount in the time between receiving the first and second signals (i.e., before moving the arm 280), the blood treatment machine console 210 recomputes the distance and direction the treatment module 220 must be moved to reduce the strain along the arterial line 102 indicated in the second signal by an amount sufficient to prevent disconnection of the blood lines 102, 104 from the dialyzer 100 or dislodgement of the needles 134, 136 from the patient 10.

Similarly, in some implementations, if the first signal received by the blood treatment machine console 210 from the venous line sensor 228 indicates strain along the venous line 104, and a second signal received from the venous line sensor 228 prior to movement of arm 280 indicates that the strain along the venous line 104 has increased, the blood treatment machine console 210 will determine whether the strain along the venous line 104 has increased more than a threshold amount. In response to detecting that the strain along the venous line 104 has increased more than a threshold amount in the time between receiving the first and second signals (i.e., before moving the arm 280), the blood treatment machine console 210 recomputes the distance and direction the treatment module 220 must be moved to reduce the strain along the venous line 104 indicated in the second signal by an amount sufficient to prevent disconnection of the blood lines 102, 104 from the dialyzer 100 or dislodgement of the needles 134, 136 from the patient 10.

In some implementations, if the first signal received by the blood treatment machine console 210 from the arterial line sensor 226 indicates strain along the arterial line 102, and the second signal received from the arterial line sensor 226 prior to movement of arm 280 indicates that there is no longer strain along the arterial line 102 or that the strain along the arterial line 102 is reduced beyond a threshold amount, this second signal can indicate that the arterial line 102 has disconnected from the dialyzer 100 or that a needle 134 coupled to the arterial line 102 has dislodged from the patient 10. For example, if the arterial line 102 has disconnected from the dialyzer 100 or the needle 134 coupling the arterial line 102 to the patient 10 has dislodged from the patient 10 (e.g., due to high levels of strain along the arterial line 102), any previously-detected strain along the arterial line will be relieved as a result of the disconnection or dislodgement. Therefore, upon determining, based on comparing the first and second signals received by the blood treatment machine console 210 from the arterial line sensor 226, that the previously-detected strain along the arterial line 102 has been eliminated or reduced prior to moving the treatment module 220, the blood treatment machine console 210 controls a pump drive unit of the treatment module 220 coupled to the pump rotor 132 to cease pumping in order to stop or pause the hemodialysis treatment. In some implementations, in response to determining, based on the second signal, that the strain along the arterial line 102 has been eliminated or reduced prior moving the treatment module 220, the blood treatment machine console 210 transmits an alert to the operator of the blood treatment machine 200 indicating a disconnection of the arterial line 102 or a dislodgement of the needle 134. In some implementations, the signal indicating reduced strain along the arterial line 102 prior to movement of arm 280 can be correlated with other sources of data, such as pumping pressure characteristics, to identifying potential disconnection of the arterial line 102 from the dialyzer 100 or dislodgement of the needle 134 coupled to the arterial line 102 from the patient 10

Similarly, if the first signal received by the blood treatment machine console 210 from the venous line sensor 228 indicates strain along the venous line 104, and the second signal received by the blood treatment machine console 210 from the venous line sensor 228 prior to movement of arm 280 indicates that there is no longer strain along the venous line 104 or that the strain along the venous line 104 has been reduced beyond a threshold amount, then it is determined that the venous line 104 has either disconnected from the dialyzer 100 or a needle 136 coupled to the venous line 104 has dislodged from the patient 10. As a result, upon determining, based on comparing the first and second signals received by the blood treatment machine console 210 from the venous line sensor 228, that the previously-detected strain along the venous line 104 has been eliminated or reduced prior to moving the treatment module 220, the blood treatment machine console 210 controls a pump drive unit of the treatment module 220 coupled to the pump rotor 132 to cease pumping in order to stop or pause movement the hemodialysis treatment. In some implementations, in response to determining, based on the second signal, that the strain along the venous line 104 has been eliminated or reduced prior moving the treatment module 220, the blood treatment machine console 210 transmits an alert to the operator of the blood treatment machine 200 indicating a disconnection of the venous line 104 or a dislodgement of the needle 136. In some implementations, the signal indicating reduced strain along the venous line 104 prior to movement of arm 280 can be correlated with other sources of data, such as pumping pressure characteristics, to identifying potential disconnection of the venous line 104 from the dialyzer 100 or dislodgement of the needle 136 coupled to the venous line 104 from the patient 10

Upon determining the direction and distance that the treatment module 220 must be moved in order to reduce the strain along the blood lines 102, 104 by an amount sufficient to prevent disconnection of the blood lines 102, 104 from the dialyzer 100 or dislodgement of the needles 134, 136 from the patient 10, the blood treatment machine console 210 controls the arm 280 to move the treatment module 220 the determined distance in the determined direction. For example, extending the arm 280 to move the treatment module 220 in the direction in which the strain is occurring along blood lines 102, 104 reduces the strain in the blood lines 102, 104 by decreasing the distance between the patient end of the blood lines 102, 104 and the treatment module 220, which creates slack in the blood lines 102, 104. In some implementations, the blood treatment machine console 210 controls the arm 280 to continue to move the treatment module 220 in the direction of the detected strain until the blood treatment machine console 210 receives a signal from the sensors 226, 228 indicating that the strain detected along the blood lines 102, 104 is below a threshold level of strain, or until the arm 280 is fully extended.

As previously discussed, the arm 280 has three degrees of motion, which allows the treatment module to be moved along each of the axes in which strain is detected by the sensors 226, 228 (e.g., X, Y, and Z planes of the arterial line 102 and X, Y, and Z planes of the venous line 104). By allowing for motion in three dimensions, the arm 280 can accurately position the treatment module 220 to alleviate strain along the blood lines 102, 104. For example, based on receiving a signal from arterial line sensor 226 indicating the components ($\varepsilon_x$, $\varepsilon_y$, and $\varepsilon_z$) of strain along the X axis, Y axis, and Z axis of the arterial line 102, the arm 280 can move the treatment module 220 the appropriate distance along each axis to alleviate the strain along the arterial line 102 detected by the arterial line sensor 226. Similarly, in response to receiving a signal from venous line sensor 228 indicating the components ($\varepsilon_x$, $\varepsilon_y$, and $\varepsilon_z$) of strain along the X axis, Y axis, and Z axis of the venous line 104, the arm 280 can move the treatment module 220 the appropriate distance along each axis to alleviate the strain along the venous line 104 detected by the venous line sensor 228.

In addition to controlling the distance and direction that the arm 280 moves to reposition the treatment module 220 in response to strain detection, the blood treatment machine console 210 can also control the speed at which the arm 280 moves to reposition the treatment module 220. For example, in response to receiving a signal from one or more of the sensors 226, 228 indicating strain along one or more of the blood lines 102, 104, the blood treatment machine console 210 can determine an appropriate speed to move the arm 280 based on the detected strain. In some implementations, the blood treatment machine console 210 controls the arm 280 to move at a speed proportional to the amount of detected strain, such that the arm 280 moves at a higher speed in response to increased levels of strain along the blood lines 102, 104. For example, high levels of strain along the blood lines 102, 104 can result in a high risk of disconnection of the respective blood line 102, 104 or dislodgement of the needles 134, 136 from the patient 10. In order to combat the increased risk of dislodgement and disconnection caused by high levels of strain along the blood lines 102, 104, the arm 280 can be controlled to move at an increased speed whenever a high level of strain is detected along the blood lines 102, 104 as compared to the speed of the arm 280 movement when a lower level of strain is detected.

After moving the arm 280 in the direction and distance determined by the blood treatment machine console 210, the blood treatment machine console 210 receives another signal from each of the sensors 226, 228. In response to receiving the second signal from the sensors 226, 228, the blood treatment machine console 210 determines whether further action is required to reduce strain along one or more of the blood lines 102, 104 by an amount sufficient to prevent disconnection of the blood lines 102, 104 from the dialyzer 100 or dislodgement of the needles 134, 136 from the patient 10. For example, if the second signal received from each of the sensors 226, 228 indicates that there is no strain along either of the blood lines 102, 104 (or indicates that the strain along the blood lines 102, 104 is below a threshold level) then the blood treatment machine console 210 ceases movement of the arm 280. Further, if the second signal received from each of the sensors 226, 228 indicates that the strain along the blood lines 102, 104 is less than a threshold amount of strain, and thus does not pose a risk of disconnection of the blood lines 102, 104 from the dialyzer 100 or dislodgement of the needles 134, 136 from the patient 10, then the blood treatment machine console 210 ceases movement of the arm 280.

However, if the second signal received by the blood treatment machine console 210 from either of the sensors 226, 228 indicates that there is still strain along one or more of the blood lines 102, 104 above a threshold amount, and thus poses a risk of disconnection of the blood lines 102, 104 from the dialyzer 100 and/or dislodgement of the needles 134, 136 from the patient 10, the blood treatment machine console 210 determines the change in strain along the blood lines 102, 104. For example, the blood treatment machine console 210 can compare the strain indicated in the first signal received from the sensor(s) 226, 228 prior to moving the treatment module 220 with the strain indicated in second signal received from the sensors(s) 226, 228 after moving the treatment module 220 in order to determine the amount of strain reduced along the blood lines 102, 104 as a result of moving the treatment module 220.

In some implementations, a change in strain along the blood lines 102, 104 resulting from movement of the treatment module 220 below a threshold amount of change indicates a snag along the respective blood line 102, 104. For example, if one of the blood lines 102, 104 is snagged or otherwise caught on an object near the blood treatment machine 200, such as the chair the patient 10 is sitting in, movement of the treatment module 220 may be ineffectual in reducing the strain along the snagged line. As such, movement of the treatment module 220 via the arm 280 may result in an amount of change in the strain along the snagged blood line 102, 104 that is less than a threshold amount of change. As a result, upon determining, based on comparing the first signal and the second signal, that the strain along one or more of the blood lines 102, 104 has decreased less than a threshold amount following repositioning of the treatment module 220, the blood treatment machine console 210 transmits an alert to an operator of the blood treatment machine 200 indicating a snag in the respective blood line(s) 102, 104. For example, in response to detecting a potential snag along a blood line 102, 104, an alert message can be displayed on the user interface 212 of the blood treatment machine 200. In some implementations, in response to detecting a potential snag along a blood line 102, 104, the blood treatment machine 200 produces an audible signal that is emitted from a speaker of the blood treatment machine 200. In some implementations, an alert message is transmitted to one or more computing devices (e.g., mobile phones, tablets, laptop computers, etc.) of the patient 10 or another user associated with the blood treatment machine 200. In some implementations, in response to determining that the strain along one or more of the blood lines 102, 104 has decreased less than a threshold amount following repositioning of the treatment module 220, the blood treatment machine console 210 controls a pump drive unit of the treatment module 220 coupled to the pump rotor 132 to cease pumping in order to stop the hemodialysis treatment.

The sensors 226, 228 continue to monitor the strain along the blood lines 102, 104 and transmit signals to the blood treatment machine console 210 in real-time throughout the hemodialysis treatment. The blood treatment machine console 210 repositions the treatment module 220 in real-time throughout the hemodialysis treatment in response to strain detected along the blood lines 102, 104 by the sensors 226, 228.

In some embodiments, once the hemodialysis treatment is complete, the blood treatment machine console 210 receives a signal indicating the completion of the treatment, and, in response, controls arm 280 to move the blood treatment module to a predetermined position. For example, receiving signals one or more sensors of the treatment module 220 indicating that the blood treatment is complete, the controller 240 can transmit a signal to the blood treatment machine console 210 indicating that the treatment is complete. In some implementations, the patient 10 or another user of the blood treatment machine 200 uses the user interface 212 of the blood treatment machine 200 to select a control indicating that the treatment is complete, and in response to this selection, the controller 240 transmits a signal to the blood treatment machine console 210 indicating that the treatment is complete. In some embodiments, after the hemodialysis treatment has been completed, an operator of the blood treatment machine 200 can use a controller 240 to adjust the position of the treatment module 220. For example, an operator of the blood treatment machine 200 can use the user interface 212 of the blood treatment machine console 210 to position the treatment module 220 in a "home position" after hemodialysis treatment has been completed. In some implementations, an operator of the blood treatment machine 200 can select an option using the user interface 212 of the blood treatment machine console 210 to position the treatment module 220 in a position close to the patient after hemodialysis treatment has been completed in order to make the disconnection of the blood lines 102, 104 from the dialyzer 100 and the patient 10 more convenient.

While certain embodiments have been described above, other embodiments are possible.

Figure 3:
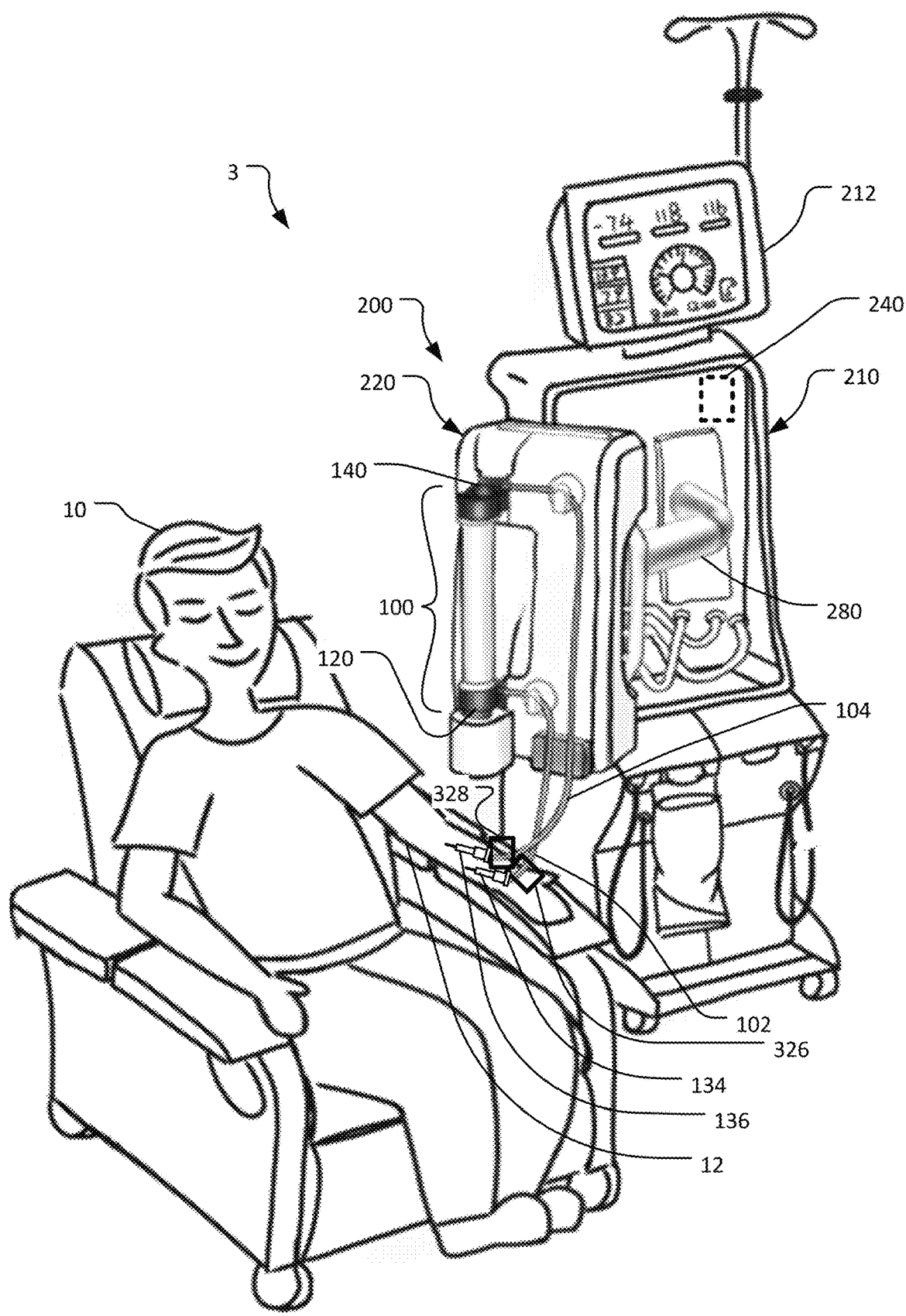
FIGS. 3-9 depict a patient receiving an extracorporeal blood treatment using alternative blood treatment systems.

For example, while the arterial line sensor 226 and the venous line sensor 228 have been described as being located on and coupled to the treatment module 220, other configurations of the strain sensors may alternatively be provided. FIG. 3, for example, illustrates a blood treatment system 3 in which an arterial line sensor 326 is positioned along and in contact with the arterial line 102 proximate an end of the arterial line 102 coupled to the needle 134 used to attach the arterial line 102 to the patient 10. Like the arterial line sensor 226 of FIG. 1, the arterial line sensor 326 is configured to detect strain along the arterial line 102 during hemodialysis treatment. Similarly, a venous line sensor 328 of the blood treatment system 3 is positioned along and in contact with the venous line 104 proximate an end of the venous line 104 coupled to the needle 136 used to attach the venous line 104 to the patient 10. The venous line sensor 328 is configured to detect strain along the venous line 104 during hemodialysis treatment. By positioning the sensors 326, 328 proximate the needles 134, 136 connecting the blood lines 102, 104 to the patient 10, the strain along the blood lines 102, 104 near the insertion point of the needles 134, 136 into the patient 10 can be more accurately detected, which allows for improved detection and prevention of dislodgement of the needles 134, 136 from the patient 10. The sensors 326, 328 can include any suitable type of sensor for detecting strain including, but not limited to, strain gauges, resistors, load cells, etc.

The sensors 326, 328 are communicably coupled to the blood treatment machine console 210 and transmit signals indicating the tension along the blood lines 102, 104 in real-time during treatment to the blood treatment machine console 210. In some implementations, the sensors 326, 328 are wireless strain sensors that communicate signals indicating the strain along the blood lines 102, 104 using any suitable form of wireless communication, including, but not limited to, WiFi, Bluetooth, etc. By wirelessly communicating with the blood treatment machine console 210 to transmit strain signals, the arterial line sensor 326 and the venous line sensor 328 can be positioned anywhere along the arterial line 102 and the venous line 104, respectively, between the treatment module 220 and the needles 134, 136. In some embodiments, the sensors 326, 328 are wired to the blood treatment machine console 210 and communicate signals to the blood treatment machine console 210 over the wiring between the sensors 326, 328 and the blood treatment machine console 210.

Figure 4:
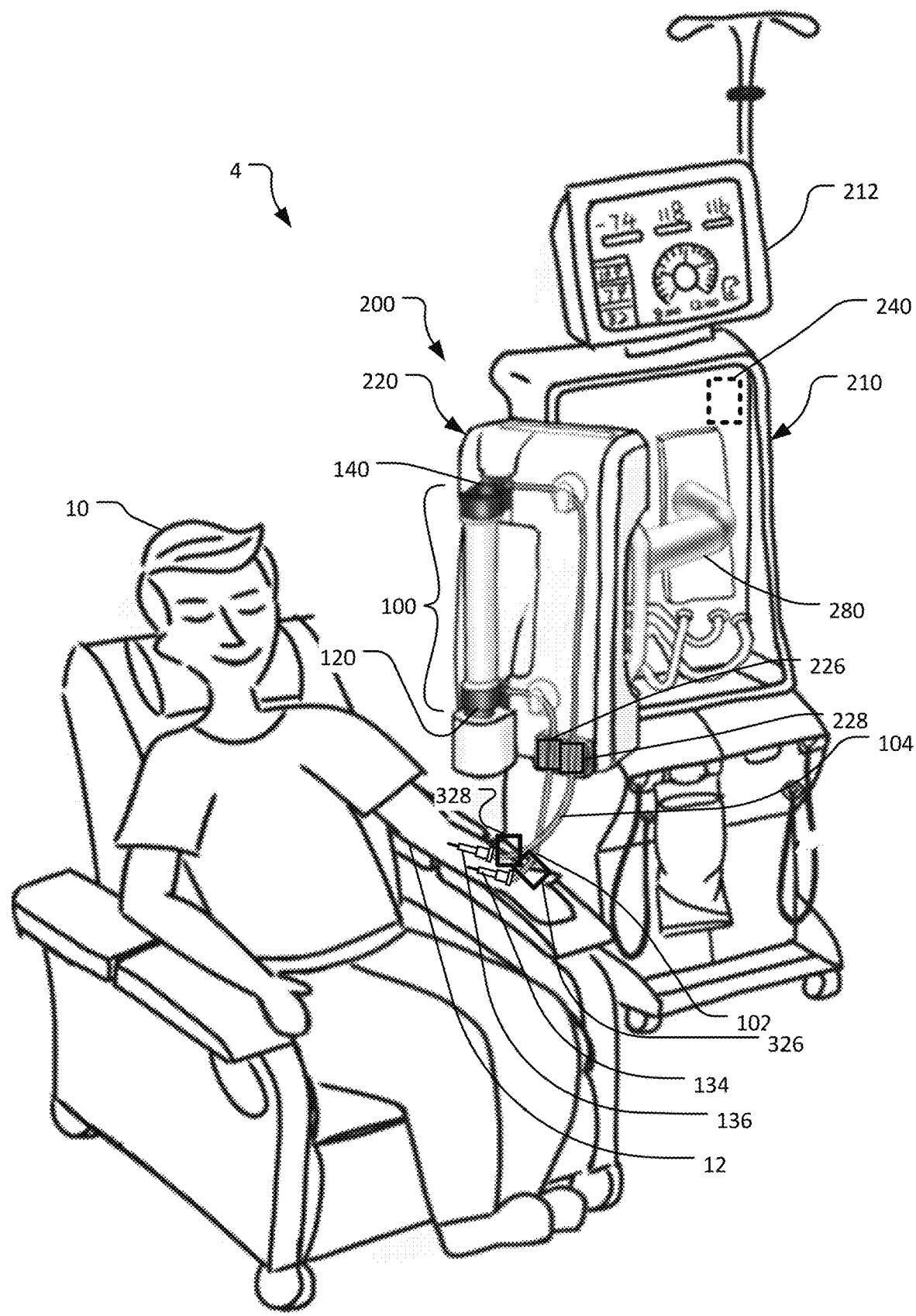

While the blood treatment system has been described as including a single arterial line sensor and a single venous line sensor, other numbers of arterial line sensors and venous line sensors can be used to monitor tension along the arterial line 102 and the venous line 104 during hemodialysis treatment. For example, FIG. 4 depicts a blood treatment system 4 that includes two arterial line sensors 226, 326 and two venous line sensors 228, 328. As depicted in FIG. 4, a first arterial line sensor 226 can be coupled to the treatment module 220. A second arterial line sensor 326 can be coupled to the arterial line 102 proximate the end of the arterial line 102 that is connected to the needle 134 attaching the arterial line 102 to the patient 10. Similarly, a first venous line sensor 228 can be coupled to the treatment module 220 and contact the venous line 104. A second venous line sensor 328 can be coupled to the venous line 104 proximate the end of the venous line 104 that is connected to the needle 136 attaching the venous line 104 to the patient 10.

As previously discussed, the arterial line sensor 326 and the venous line sensor 328 positioned along the blood lines 102, 104 near the patient ends of the blood lines 102, 104 can be wireless sensors configured to transmit signals indicating the strain along the blood lines 102, 104 wirelessly to the blood treatment machine console 210. In contrast, the arterial line sensor 226 and the venous line sensor 228 coupled to the treatment module 220 can be electrically wired to the treatment module 220 and/or the blood treatment machine console 210 and transmit signals indicating the strain along the blood lines 102, 104 to the blood treatment machine console 210 via the wired connections between the sensors 226, 228 and the blood treatment machine console 210. Alternatively, all of the strain sensors 226, 228, 326, 328 can be wireless strain sensors configured to transmit signals indicating the strain along the blood lines 102, 104 wirelessly to the blood treatment machine console 210. In some of the embodiments, all of the strain sensors 226, 228, 326, 328 are electrically wired to the treatment module 220 and/or the blood treatment machine console 210.

While the arterial line sensor and the venous line sensor have been depicted in FIGS. 1, 3, and 4 as being in contact with the surface of the arterial line 102 and venous line 104, in some embodiments, the arterial line sensor and venous line sensor are embedded into the blood lines 102, 104 to measure strain along the respective blood lines 102, 104. For example, the arterial line sensor and the venous line sensor can each be provided as wireless strain sensors that are embedded or otherwise fabricated into the blood lines 102, 104, respectively. As the blood lines 102, 104 are subjected to strain, the embedded strain sensors detect and measure the strain along the blood lines 102, 104, and wirelessly transmit the detected strain along the blood lines 102, 104 to the blood treatment machine console 210. In some implementations, the blood lines 102, 104 can each include embedded conductive material that forms a strain gauge along the length of each of the blood lines 102, 104, and based on the measuring the strain experienced by the conductive material, strain can be detected along the length of each of the blood lines 102, 104. In some implementations, a conductive coating or conductive outer layer is applied along the length of each of the blood lines 102, 104, and based on the measuring the strain experienced by the conductive coating or conductive outer layer, strain can be detected along the length of each of the blood lines 102, 104.

Further, while the blood treatment system has been described as including strain sensors that are coupled to or embedded in the blood lines 102, 104, the strain sensors of the blood treatment system can alternatively or additionally be positioned to contact other portions of the blood treatment system. For example, as depicted in FIG. 5, a blood treatment system 5 can include strain sensors 526, 528 that are coupled to and positioned within one or more joints of the arm 280 coupled to the treatment module 220, and are configured to measure strain applied to one or more of the blood lines 102, 104.

Figure 5:
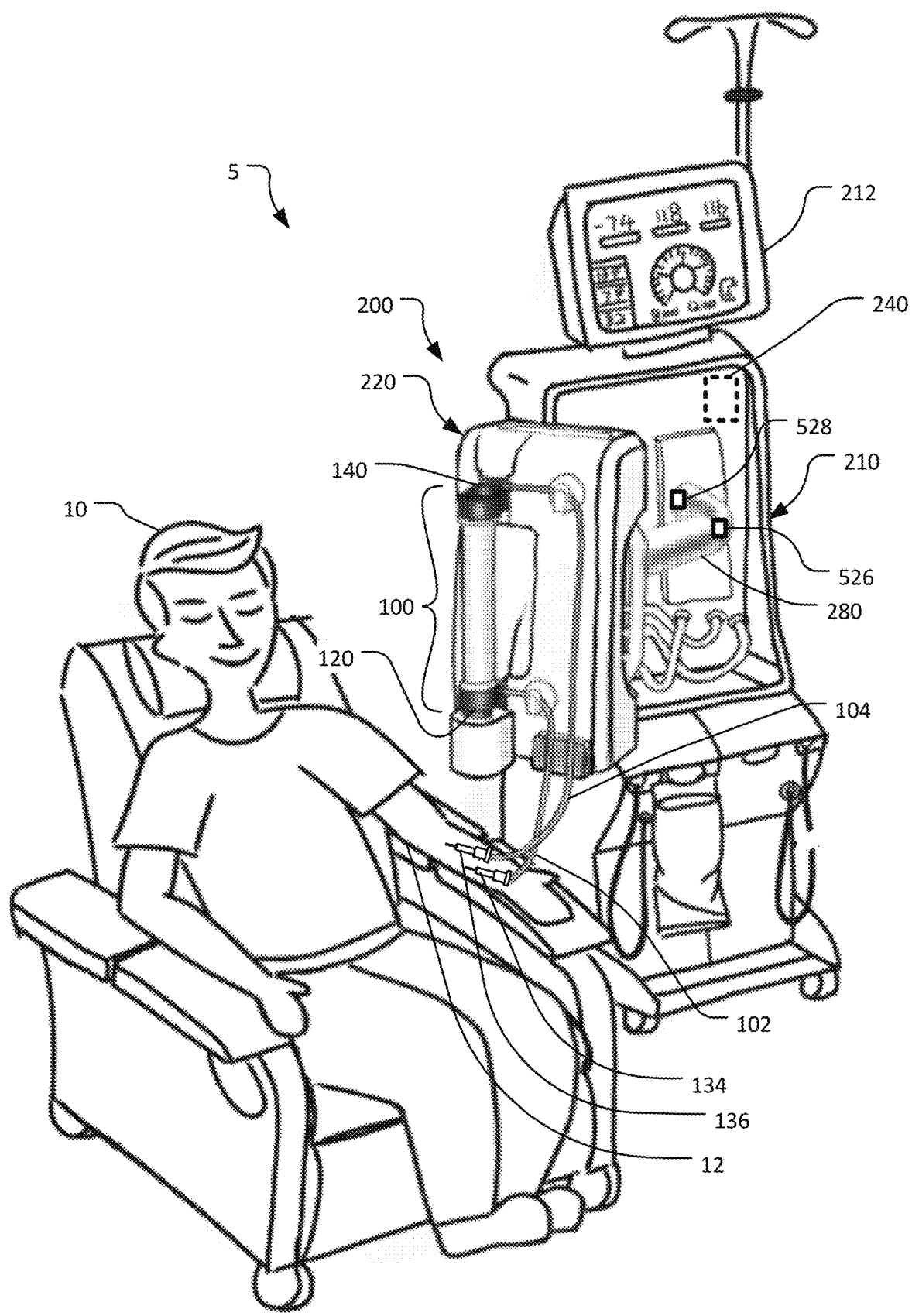

As can be seen in FIG. 5, and as previously discussed, the blood lines 102, 104 of the blood treatment system 5 are each attached to the dialyzer 100, which is attached to the treatment module 220, and the treatment module 220 is coupled to the arm 280. As such, when strain occurs along the blood lines 102, 104 (e.g., due to movement of the arm 12 of the patient 10), at least some of the force causing strain along the blood lines 102, 104 is transferred to the dialyzer 100 and the treatment module 220, which then transfers at least some of the force to the arm 280. The strain sensors 526, 528 are configured to detect the force applied to the joints of the arm 280, and transmit signals to the blood treatment machine console 210 indicating the force being applied to the joints of the arm 280. The blood treatment machine console 210 can apply a predetermined relationship between strain along the blood lines 102, 104 and the force transferred to the joints of the arm 280 to the signals received from the sensors 256, 258 in order to determine the strain along the blood lines 102, 104 based on the sensor signals. Based on this determination of strain along the blood lines 102, 104, the blood treatment machine console 210 can determine the direction and distance the treatment module 220 must be moved to in order to reduce the detected strain along the blood line(s) 102, 104 by an amount sufficient to prevent disconnection of the blood lines 102, 104 from the dialyzer 100 or dislodgement of the needles 134, 136 from the patient 10, as described above.

While FIG. 5 depicts two strain sensors 526, 528 coupled to the joints of the arm 280 of the blood treatment machine 200, other numbers of strain sensors coupled to the arm 280 can be used. For example, the system 5 may include a strain sensor in each joint of the arm 280 such that the number of strain sensors is equal to the total number of joints in the arm 280. In some implementations, the blood treatment system 5 can include strain sensors in contact with the blood lines 102, 104, as well as strain sensors 256, 258 coupled to the joints of the arm 280.

While the sensors for detecting tension along the blood lines 102, 104 have been described as being strain sensors, other types of sensors can be used to detect tension along the blood lines 102, 104 of the blood treatment system. FIGS. 6-9 depict schematics of alternate blood treatment systems with one or more sensors used for detecting tension along one or more blood lines.

Figure 6:
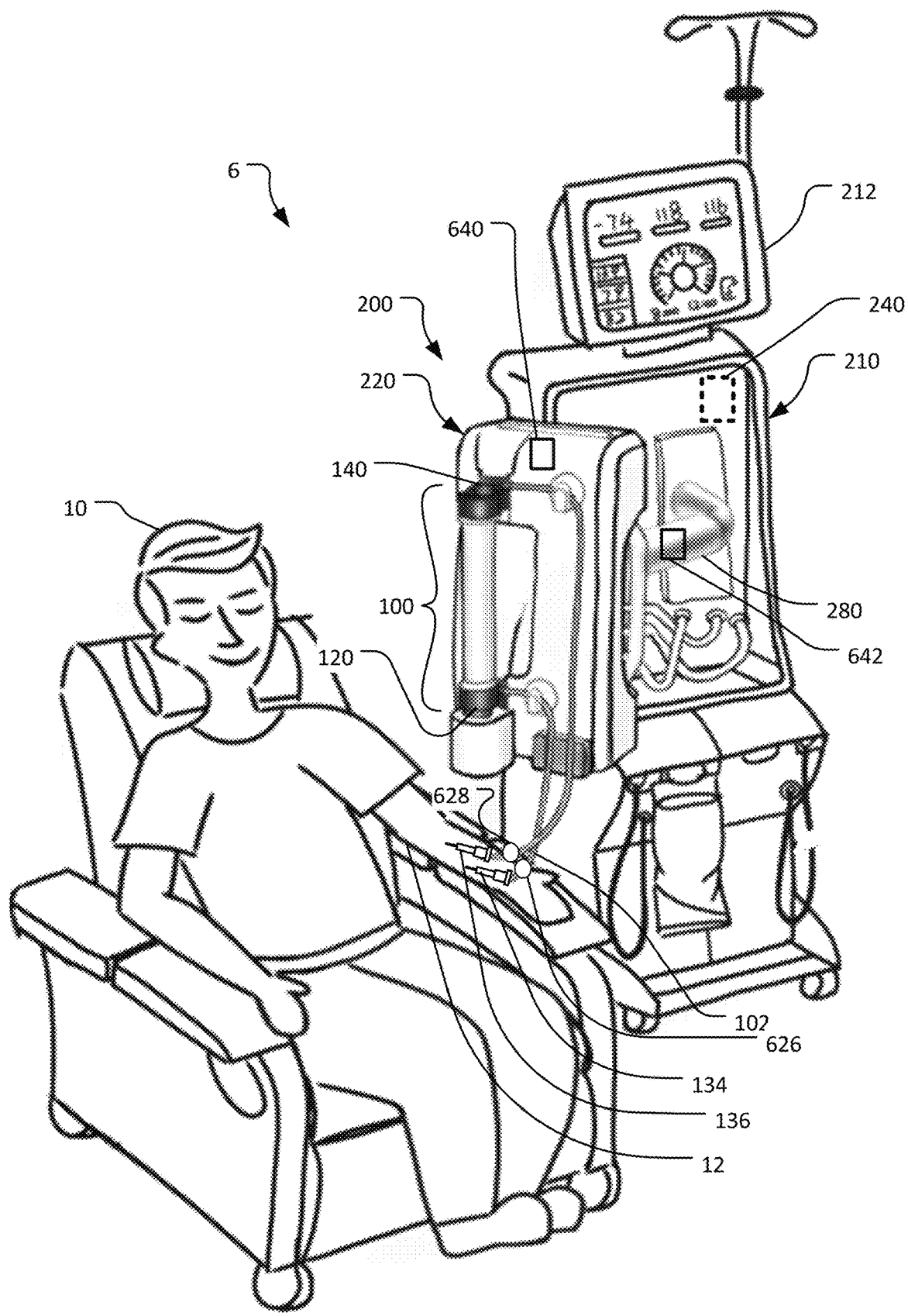

In some implementations, rather than using strain sensors to detect tension in the blood lines 102, 104, the blood treatment system can include one or more sensors configured to detect the position of a portion of the blood lines 102, 104 in order to determine tension along the blood lines 102, 104. For example, as depicted in FIG. 6, a blood treatment system 6 can include a pair of sensors 626, 628 attached to the blood lines 102, 104 that are configured to detect the position of the portions of the blood lines 102, 104 coupled to the sensors 626, 628. The sensors 626, 628 can be any suitable type of sensor for detecting the position and/or movement of the blood lines 102, 104, including, but not limited to, accelerometers (e.g., 3D accelerometers), gyroscopic sensors, ultrasonic sensors, proximity sensors, optical sensors, magnetometers, global positioning sensors, radio triangulation sensors (e.g., like in keyless access systems for cars or based on WiFi, Bluetooth or similar technologies), and the like. The sensors 626, 628 are communicably coupled to the blood treatment machine console 210 and are configured to transmit signals to the blood treatment machine console 210 in real-time during hemodialysis treatment indicating the position, orientation, and/or motion of the portion of the blood lines 102, 104 proximate the sensors 626, 628. In some implementations, the sensors 626, 628 are configured to detect the position of the portions of the blood lines 102, 104 coupled to the sensors 626, 628 in three dimensional space, and transmit coordinates indicating the position of the portions of the blood lines 102, 104 coupled to the sensors 626, 628 in three dimensional space to the blood treatment machine console 210.

For example, the first sensor 626 can be an accelerometer attached to the arterial line 102 proximate an end of the arterial line 102 coupled to the needle 134 connecting the arterial line 102 to the patient 10. The second sensors 628 can be an accelerometer attached to the venous line 104 proximate an end of the venous line 104 coupled to the needle 136 connecting the venous line 104 to the patient 10. The sensors 626, 628 are configured to detect movement of the portions of the arterial line 102 and venous line 104, respectively, proximate the sensors 626, 628. For example, if the patient 10 moves his arm 12, the ends of the blood lines 102, 104 proximate the sensors 626, 628 will move as a result, and this movement of the blood lines 102, 104 will be detected by the sensors 626, 628. In some implementations, the sensors 626, 282 are configured to detect both the speed and the direction of the movement the portions of the blood lines 102, 104 proximate the sensors 626, 628.

The sensors 626, 628 transmit a signal indicating the position and the speed and direction of movement of the portions of the blood lines 102, 104 proximate the sensors 626, 628 to the blood treatment machine console 210 in real-time during hemodialysis. In response, the blood treatment machine console 210 can determine the amount of strain along each of the blood lines 102, 104 based on the signals received from the sensors 626, 286 indicating the position and the movement of the blood lines 102, 104. For example, based on the position of the portions of the blood lines 102, 104 proximate the sensors 626, 628 relative to the position of the treatment module 220, the distance between the portions of the blood lines 102, 104 proximate the sensors 626, 628 and the treatment module 220 can be determined. In some implementations, the blood treatment machine console 210 determines the position of the treatment module 220 based on one or more position sensors 640, 642 coupled to the treatment module 220 and/or the arm 280. Based on the determined distance between the portions of the blood lines 102, 104 proximate the sensors 626, 628 and the position of the treatment module 220, and the length of the blood lines 102, 104 between the sensors 626, 628 and the treatment module 220, the blood treatment machine console 210 can determine the amount of strain occurring along the blood lines 102, 104.

Based on this determination of strain along the blood lines 102, 104, the blood treatment machine console 210 can determine a distance and direction that the treatment module 220 must be moved to in order to reduce the detected strain along the blood line(s) 102, 104 by an amount sufficient to prevent disconnection of the blood lines 102, 104 from the dialyzer 100 or dislodgement of the needles 134, 136 from the patient 10, as described above. In some implementations, in response to detecting movement of the portions of the blood lines 102, 104 proximate the sensors 626, 628, the blood treatment machine console 210 automatically controls the arm 280 to move the treatment module 220 towards the detected position of the portions of the blood lines 102, 104 proximate the sensors 626, 628 in order to generate slack in the blood lines 102, 104.

In some implementations, the risk of disconnection of the blood lines 102, 104 from the dialyzer 100 or dislodgement of the needles 134, 136 from the patient 10 is determined based on the distance detected between the position sensors 626, 628 and the position of the treatment module 220, without requiring a calculation of the strain along the blood lines 102, 104. For example, as previously discussed, based on the signals received from the position sensors 626, 628, 640, 642, the blood treatment machine console 210 can determine the distance between the portions of the blood lines 102, 104 proximate the sensors 626, 628 and the treatment module 220 in one or more planes in real-time during treatment. In some implementations, if the blood treatment machine console 210 determines that the distance between the portions of the blood lines 102, 104 proximate the sensors 626, 628 and the treatment module 220 exceeds a threshold distance associated with an increased risk of dislodgement or disconnection of the blood lines 102, 104, the blood treatment machine console 210 automatically controls the arm 280 to move the treatment module 220 towards the detected position of the portions of the blood lines 102, 104 proximate the sensors 626, 628. For example, the blood treatment machine console 210 can control the arm 280 to move the treatment module 220 towards the detected position of the portions of the blood lines 102, 104 proximate the sensors 626, 628 until the distance between the portions of the blood lines 102, 104 proximate the sensors 626, 628 and the treatment module 220 is less than the threshold distance.

In some implementations, based the signals received from the sensors 626, 628, the blood treatment machine console 210 can predict future movement of the portions of the blood lines 102, 104 proximate the sensors 626, 628. Based on this predicted movement, the blood treatment machine console 210 can control the arm 280 to move the treatment module 220 in a direction that counteracts any increased strain that could be caused by the predicted movement.

While FIG. 6 depicts two position sensors 626, 628 coupled to the blood lines 102, 104, other numbers of position sensors 626, 628 can be used to determine the position, orientation, and/or motion of the blood lines 102, 104. In addition, while FIG. 6 depicts the position sensors 626, 628 as being coupled to portions of the blood lines 102, 104 proximate the patient end of the blood lines 102, 104, the position sensors may be positioned at other points along the blood lines 102, 104.

Figure 7:
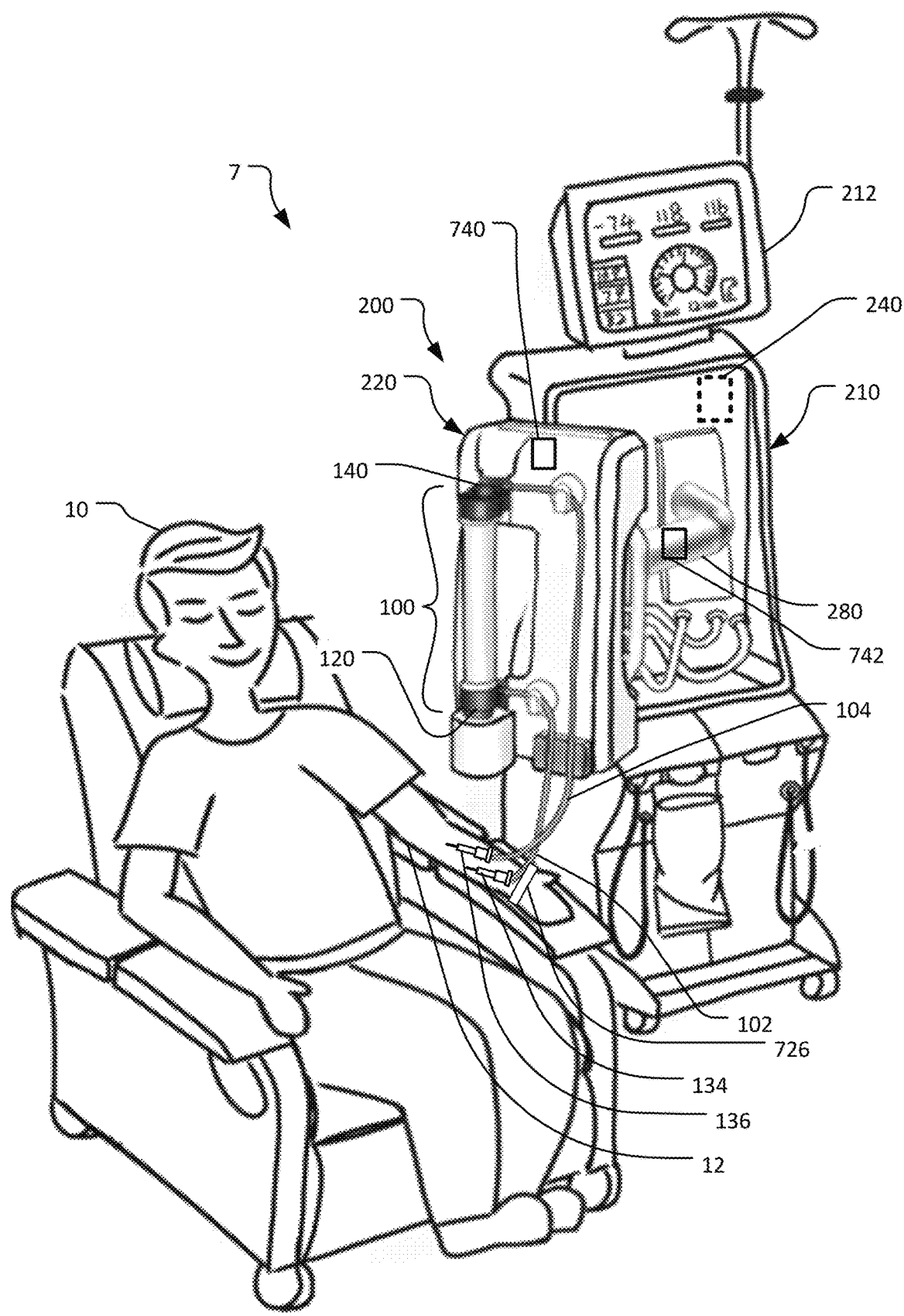

In some implementations, rather than having strain sensors coupled to the blood lines 102, 104, the blood treatment system includes a position sensor attached to the arm 12 of the patient 10 that is configured to track the position of the patient's arm 12, and the tension along the blood lines 102, 104 is determined based on the position of the patient's arm 12. For example, as depicted in FIG. 7, the patient 10 can wear or otherwise attach a wearable position device 726 on his arm 12 during a hemodialysis treatment carried out by a blood treatment system 7. The wearable position device 726 can be any suitable type of sensor for detecting the position and/or movement of the patient's arm 12, including, but not limited to, accelerometers (e.g., 3D accelerometers), gyroscopic sensors, ultrasonic sensors, proximity sensors, optical sensors, magnetometers, global positioning sensors, radio triangulation sensors (e.g., like in keyless access systems for cars or based on WiFi, Bluetooth or similar technologies), fitness trackers, smart watches, and the like.

The wearable position device 726 is configured to wirelessly transmit signals indicating the position, orientation, and/or movement of the patient's arm 12 to the blood treatment machine console 210 in real-time during hemodialysis treatment. For example, in some implementations, the wearable position device 726 is configured to wirelessly transmit signals indicating the position, orientation, and/or movement of the patient's arm 12 to the blood treatment machine console 210 using near-field communication. In some implementations, the wearable position device 726 is configured to detect the position of a portion of the patient's arm 12 proximate the wearable position device 726 (e.g., the patient's wrist) in three dimensional space, and transmit coordinates indicating the position in three dimensional space of the portion of the patient's arm 12 proximate the wearable position device 726 to the blood treatment machine console 210 in real-time.

Based on the signals received from the wearable position device 726, the blood treatment machine console 210 can detect or predict tension along the blood lines 102, 104. For example, once the blood lines 102, 104 are attached to the treatment module 220 and to the patient's arm 12 (via needles 134, 136), movement of the patient's arm 12 away from the treatment module 220 can result in increased tension along the blood lines 102, 104. As such, by tracking the position of the patient's arm 12 using a wearable position device 726 on the patient's wrist during hemodialysis, the tension along the blood lines 102, 104 can be detected or predicted.

For example, based on the position of the portion of the patient's arm 12 proximate wearable position device 726 relative to the position of the treatment module 220, and based on a known or approximated distance between the wearable position device 726 and the patient ends of each of the blood lines 102, 104, the distance between the patient ends of each of the blood lines 102, 104 and the treatment module 220 can be determined from signals received from the wearable position device 726. As previously discussed, the blood treatment machine console 210 can determine the position of the treatment module 220 based on one or more position sensors 740, 742 coupled to the treatment module 220 and/or the arm 280. Based on the determined distance between the patient ends of each of the blood lines 102, 104 and the treatment module 220, and the predetermined length of the blood lines 102, 104 between patient ends of the blood lines 102, 104 and the treatment module 220, the blood treatment machine console 210 can determine the amount of strain occurring along the blood lines 102, 104

Based on this determination of strain along the blood lines 102, 104, the blood treatment machine console 210 can determine a distance and direction that the treatment module 220 must be moved to in order to reduce the strain along the blood line(s) 102, 104 by an amount sufficient to prevent disconnection of the blood lines 102, 104 from the dialyzer 100 or dislodgement of the needles 134, 136 from the patient 10, as described above. In some implementations, in response to detecting that the patient 10 has moved his arm 12 away from the treatment module 220 during hemodialysis treatment based on signals received from the wearable position device 726, the blood treatment machine console 210 automatically controls the arm 280 to move the treatment module 220 towards the patient 10 (e.g., towards the detected position of the wearable position device 726) in order to generate slack in the blood lines 102, 104.

In some implementations, the risk of disconnection of the blood lines 102, 104 from the dialyzer 100 or dislodgement of the needles 134, 136 from the patient 10 is determined based on the distance detected between the wearable position device 726 and the position of the treatment module 220, without requiring a calculation of the strain along the blood lines 102, 104. For example, as previously discussed, based on the known or approximated distance between the wearable position device 726 and the patient ends of each of the blood lines 102, 104, the signals received from the wearable position device 726, and the signals received from the position sensors 740, 742, the blood treatment machine console 210 can determine the distance between the patient ends of each of the blood lines 102, 104 and the treatment module 220 in one or more planes in real-time during treatment. In some implementations, if the blood treatment machine console 210 determines that the distance between the patient ends of each of the blood lines 102, 104 and the treatment module 220 exceeds a threshold distance associated with an increased risk of dislodgement or disconnection of the blood lines 102, 104, the blood treatment machine console 210 automatically controls the arm 280 to move the treatment module 220 towards the detected position of the wearable position device 726. For example, the blood treatment machine console 210 can control the arm 280 to move the treatment module 220 towards the detected position of the wearable position device 726 until the distance between the patient ends of each of the blood lines 102, 104 (as determined based on the position of the wearable position device 726) and the treatment module 220 is less than the threshold distance.

In some implementations, based the signals received from the wearable position device 726 and based on a known or approximated distance between the wearable position device 726 and the patient ends of each of the blood lines 102, 104, the blood treatment machine console 210 can predict future movement of the patient ends of each of the blood lines 102, 104. Based on this predicted movement, the blood treatment machine console 210 can control the arm 280 to move the treatment module 220 in a direction that counteracts any increased strain that could be caused by the predicted movement.

Figure 8:
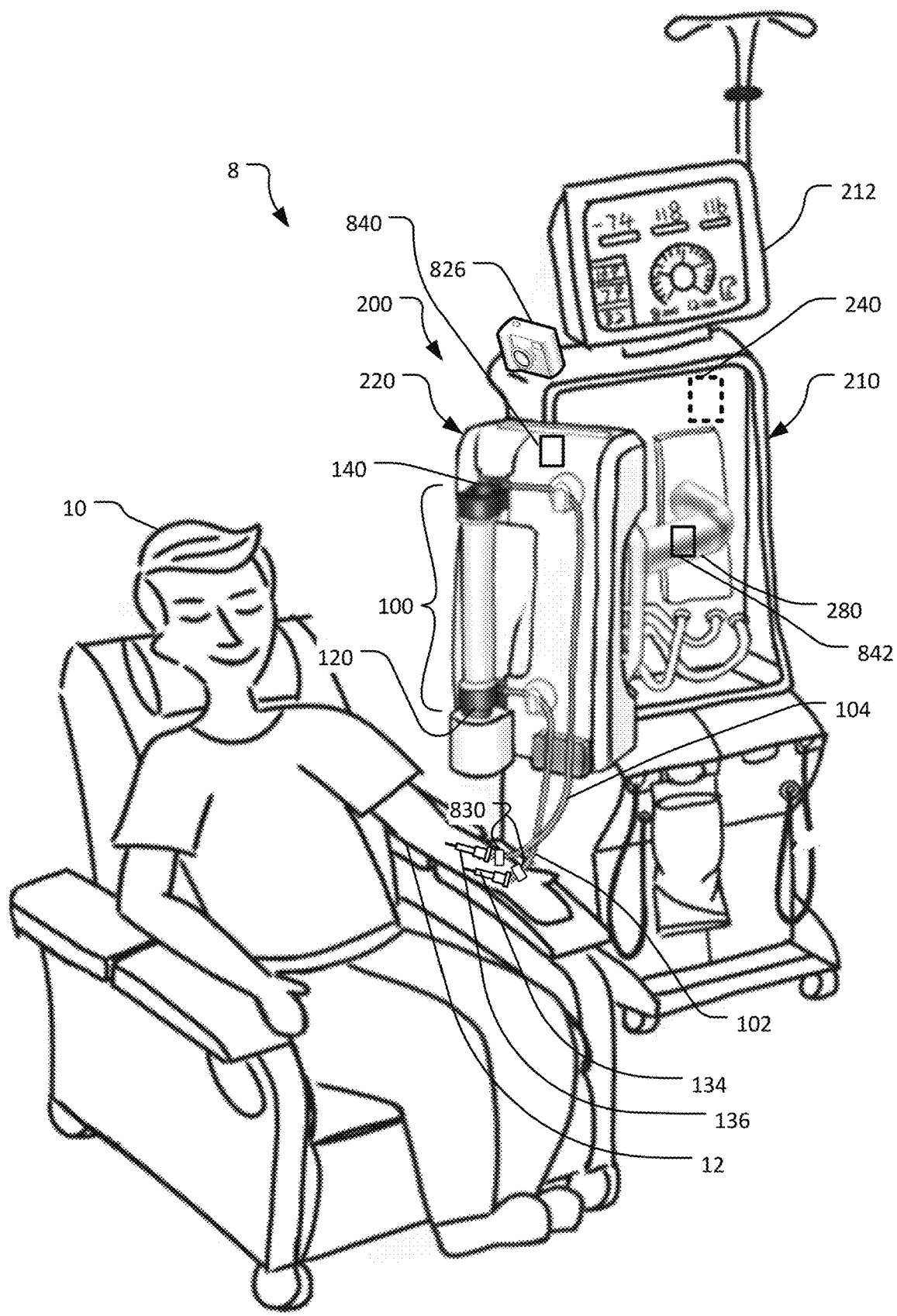

In some implementations, an image sensor may be used to determine or predict tension along the blood lines 102, 104 of the blood treatment system. For example, as depicted in FIG. 8, in some implementations, the blood treatment system 8 includes an image sensor 826 that can be used to track a portion of the patient's arm 12 in order to detect or predict tension along the blood lines 102, 104. As can be seen in FIG. 8, the blood treatment system 8 includes an image sensor 826 that is positioned on the blood treatment machine console 210 and is directed towards the arm 12 of the patient 10. In addition, a passive device 830 used to reflect light is positioned on the arm 12 of the patient 10. The passive device 830 can include any suitable device or material that reflects infrared light, including, but not limited to, reflective tape, retroreflectors, etc. For example, the passive device 830 can include reflective tape that is used to tape down and secure the needles 134, 136 to the arm 12 of the patient 10. The image sensor 826 can include any acceptable image sensor configured to detect reflected infrared light, including, but not limited to, an infrared sensor, a digital camera, a thermographic camera, a video camera, a camcorder, etc.

During hemodialysis treatment, the image sensor 826 tracks the infrared light reflected by the passive device 830 positioned on the patient's arm 12. The image sensor 826 is configured to transmit in real-time to the blood treatment machine console 210, via a wired connection or a wireless connection, signals indicating the pattern of light reflected by the passive device 830 and detected by the image sensors 826. Based on the pattern of light reflected off the passive device 830, as detected by the image sensor 826, the blood treatment machine console 210 can determine the location of the portion of the patient's arm 12 proximate the passive device 830.

By tracking the position of the patient's arm 12 relative to the position of the treatment module 220 during hemodialysis treatment using an image sensor 826 tracking reflected light patterns produced by a passive device 830 on the patient's arm 12, the strain along the blood lines 102, 104 can be detected. For example, based on the position of the portion of the patient's arm 12 proximate passive device 830 relative to the position of the treatment module 220, and based on a known or approximated distance between the passive device 830 and the patient ends of each of the blood lines 102, 104, the distance between the patient ends of each of the blood lines 102, 104 and the treatment module 220 can be determined. As previously discussed, the blood treatment machine console 210 can determine the position of the treatment module 220 based on one or more position sensors 840, 842 coupled to the treatment module 220 and/or the arm 280. Based on the determined distance between the patient ends of each of the blood lines 102, 104 and the treatment module 220, and the predetermined length of the blood lines 102, 104 between patient ends of the blood lines 102, 104 and the treatment module 220, the blood treatment machine console 210 can determine the amount of strain occurring along the blood lines 102, 104.

Based on this determination of strain along the blood lines 102, 104, the blood treatment machine console 210 can determine a distance and direction that the treatment module 220 must be moved to in order to reduce the detected strain along the blood line(s) 102, 104 by an amount sufficient to prevent disconnection of the blood lines 102, 104 from the dialyzer 100 or dislodgement of the needles 134, 136 from the patient 10, as described above. In some implementations, in response to detecting that the patient 10 has moved his arm 12 away from the treatment module 220 during hemodialysis treatment based on signals from the image sensor 826, the blood treatment machine console 210 automatically controls the arm 280 to move the treatment module 220 towards the patient's arm 12 (e.g., towards the detected position of the passive device 830) in order to generate slack in the blood lines 102, 104.

In some implementations, the risk of disconnection of the blood lines 102, 104 from the dialyzer 100 or dislodgement of the needles 134, 136 from the patient 10 is determined based on the distance detected between the patient ends of the blood lines 102, 104 and the position of the treatment module 220, without detected strain along the blood lines 102, 104. For example, as previously discussed, based on the known or approximated distance between the passive device 830 and the patient ends of each of the blood lines 102, 104, the signals from the image sensor 826 indicating the position of the passive device 830, and the signals received from the position sensors 840, 842, the blood treatment machine console 210 can determine the distance between the patient ends of the blood lines 102, 104 and the treatment module 220 in one or more planes in real-time during treatment. In some implementations, if the blood treatment machine console 210 determines that the distance between the patient ends of the blood lines 102, 104 and the treatment module 220 exceeds a threshold distance that is associated with an increased risk of dislodgement or disconnection of the blood lines 102, 104, the blood treatment machine console 210 automatically controls the arm 280 to move the treatment module 220 towards the detected position of the passive device 830. For example, the blood treatment machine console 210 can control the arm 280 to move the treatment module 220 towards the detected position of the passive device 830 until the distance between the patient ends of each of the blood lines 102, 104 (as determined based on the position of the passive device 830) and the treatment module 220 is less than the threshold distance.

In some implementations, based the signals received from the image sensor 826 and based on a known or approximated distance between the passive device 830 and the patient ends of each of the blood lines 102, 104, the blood treatment machine console 210 can predict future movement of the patient ends of each of the blood lines 102, 104. Based on this predicted movement, the blood treatment machine console 210 can control the arm 280 to move the treatment module 220 in a direction that counteracts any increased strain that could be caused by the predicted movement.

While FIG. 8 depicts the passive device 830 as being positioned on the arm 12 of the patient 10, the passive device 830 can alternatively or additionally be positioned on other surfaces. For example, in some implementations, a passive device 830, such as reflective material, may be positioned on or embedded into a portion of each of the blood lines 102, 104, and the image sensor 826 can be used to track the position of the blood lines 102, 104 to detect tension in the blood lines 102, 104.

While the passive device 830 has been described as being a reflective material, in some embodiments the passive device is color keyed and the image sensor 826 is configured to detect and track the color of the passive device. For example, the image sensor 826 can be configured to transmit in real-time to the blood treatment machine console 210, via a wired connection or a wireless connection, signals indicating the location of the passive device 830 as detected by the image sensor 826 based on the color of the passive device.

In addition, while FIG. 8 depicts the image sensor 826 as being positioned on the blood treatment machine console 210, the image sensor 826 can be positioned on other portions of the blood treatment system 8. For example, in some implementations, the image sensor 826 is coupled to or integrated into the treatment module 220. In some implementations, the image sensor 826 is coupled to the chair the patient 10 sits in during treatment. Further, while FIG. 8 depicts a single image sensor 826, other numbers of image sensors 826 may be used.

Figure 9:
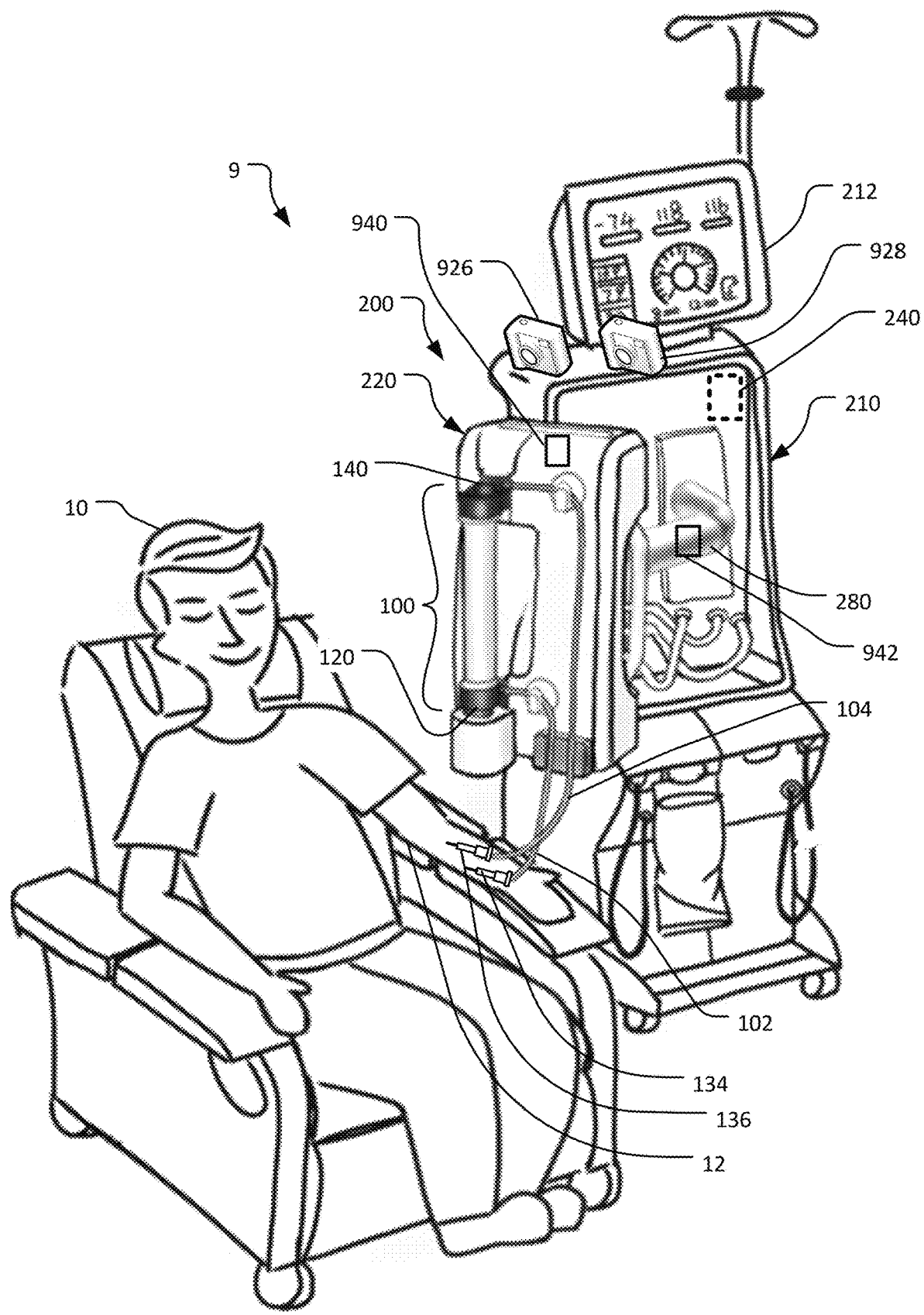

As depicted in FIG. 9, for example, a blood treatment system 9 includes image sensors 926, 928 that track the position of one or more objects attached to or near the blood treatment machine 200 in order to detect or predict tension along the blood lines 102, 104. For example, the image sensors 926, 928 can capture images of the patient 10 and/or the blood lines 102, 104 during hemodialysis treatment, and transmit the images to a computing device of the blood treatment machine console 210 (e.g., controller 240). The computing device of the blood treatment machine console 210 can process the images received from the image sensors 926, 928 using a trained machine learning model to detect the position of the patient 10 and/or the blood lines 102, 104 based on the images captured by the image sensors 926, 928. The image sensors 926, 928 can include any acceptable image sensors configured to capture images, including, but not limited to, digital cameras, video cameras, camcorders, etc.

For example, as depicted in FIG. 9, the image sensors 926, 928 can be positioned on the blood treatment machine console 210 and configured to capture images of the patient's arm 12 throughout a hemodialysis treatment. The images of the patient's arm 12 captured by the image sensors 926, 928 are communicated in real-time to a computing device of the blood treatment machine console 210 via a wired or wireless connection. The computing device of the blood treatment machine console 210 processes the images of the patient's arm 12 received from the image sensors 926, 928 using a trained machine learning model to determine the position of the patient's arm 12 in three dimensional space. Based on determining the position of the detected portion of the patient's arm 12 relative to the position of the treatment module 220, and based on a known or approximated distance between the detected portion of the patient's arm 12 and the patient ends of each of the blood lines 102, 104, the distance between the patient ends of each of the blood lines 102, 104 and the treatment module 220 can be determined. As previously discussed, the blood treatment machine console 210 can determine the position of the treatment module 220 based on one or more position sensors 940, 942 coupled to the treatment module 220 and/or the arm 280. Based on the determined distance between the patient ends of each of the blood lines 102, 104 and the treatment module 220, and the predetermined length of the blood lines 102, 104 between patient ends of the blood lines 102, 104 and the treatment module 220, the blood treatment machine console 210 can determine the amount of strain occurring along the blood lines 102, 104.

Based on this determination of strain along the blood lines 102, 104, the blood treatment machine console 210 can determine a distance and direction that the treatment module 220 must be moved to in order to reduce the detected strain along the blood line(s) 102, 104 by an amount sufficient to prevent disconnection of the blood lines 102, 104 from the dialyzer 100 or dislodgement of the needles 134, 136 from the patient 10, as described above. In some implementations, in response to detecting that the patient 10 has moved his arm 12 away from the treatment module 220 during hemodialysis treatment based on signals from the image sensors 926, 928 the blood treatment machine console 210 automatically controls the arm 280 to move the treatment module 220 towards the patient 10 (e.g., towards the detected position of the patient's arm 12) in order to generate slack in the blood lines 102, 104.

In some implementations, the image sensors 926, 928 can be used to track the position of the blood lines 102, 104 in order to determine tension along the blood lines 102, 104. For example, the image sensors 926, 928 can be positioned on the blood treatment machine console 210 and configured to capture images of the end of each of the blood lines 102, 104 coupled to the needles 134, 136 (i.e., the "patient end" of the blood lines 102, 104) throughout the hemodialysis treatment. The images of the patient end of each of the blood lines 102, 104 captured by the image sensors 926, 928 are communicated in real-time to a computing device of the blood treatment machine console 210 via a wired or wireless connection. The computing device of the blood treatment machine console 210 processes the images of the patient end of each of the blood lines 102, 104 received from the image sensors 926, 928 using a trained machine learning model to determine the position of the patient end of each of the blood lines 102, 104 in three dimensional space. As previously discussed, based on determining the position of the patient end of each of the blood lines 102, 104 relative to the position of the treatment module 220, and based on the predetermined length of the blood lines 102, 104 between patient ends of the blood lines 102, 104 and the treatment module 220, the blood treatment machine console 210 can determine the amount of strain occurring along the blood lines 102, 104.

Based on this determination of strain along the blood lines 102, 104, the blood treatment machine console 210 can determine a distance and direction that the treatment module 220 must be moved to in order to reduce the detected strain along the blood line(s) 102, 104 by an amount sufficient to prevent disconnection of the blood lines 102, 104 from the dialyzer 100 or dislodgement of the needles 134, 136 from the patient 10, as described above. In some implementations, in response to determining that the patient ends of the blood lines 102, 104 have been moved away from the treatment module 220 based on signals from the image sensors 926, 928 the blood treatment machine console 210 automatically controls the arm 280 to move the treatment module 220 towards the detected position of the patient ends of the blood lines 102, 104 in order to generate slack in the blood lines 102, 104.

In some implementations, the risk of disconnection of the blood lines 102, 104 from the dialyzer 100 or dislodgement of the needles 134, 136 from the patient 10 is determined based on the distance detected between the patient ends of the blood lines 102, 104 and the position of the treatment module 220, without requiring a calculation of the strain along the blood lines 102, 104. For example, as previously discussed, based on the signals received from the image sensors 926, 928 indicating the position of the patient ends of the blood lines 102, 104, and the signals received from the position sensors 940, 942, the blood treatment machine console 210 can determine the distance between the patient ends of the blood lines 102, 104 and the treatment module 220 in one or more planes in real-time during treatment. In some implementations, if the blood treatment machine console 210 determines that the distance between the patient ends of the blood lines 102, 104 and the treatment module 220 exceeds a threshold distance associated with an increased risk of dislodgement or disconnection of the blood lines 102, 104, the blood treatment machine console 210 automatically controls the arm 280 to move the treatment module 220 towards the detected position of patient ends of the blood lines 102, 104. For example, the blood treatment machine console 210 can control the arm 280 to move the treatment module 220 towards the detected position of the patient ends of the blood lines 102, 104 until the distance between the patient ends of each of the blood lines 102, 104 and the treatment module 220 is less than the threshold distance.

In some implementations, based the signals received from the image sensor 926, the blood treatment machine console 210 can predict future movement of the patient ends of each of the blood lines 102, 104. Based on this predicted movement, the blood treatment machine console 210 can control the arm 280 to move the treatment module 220 in a direction that counteracts any increased strain that could be caused by the predicted movement.

While FIG. 9 depicts the image sensors 926, 928 as being positioned on the blood treatment machine console 210, one or more of the image sensors 926, 928 can be positioned on other portions of the blood treatment system 9. For example, in some implementations, one or more of the image sensors 926, 928 are coupled to or integrated into the treatment module 220. In some implementations, one or more of the image sensors 926, 928 are coupled to the chair the patient 10 sits in during treatment. Further, while FIG. 9 depicts two image sensors 926, 928, other numbers of image sensors 926, 928 may be used. In addition, while the image sensors 926, 928 have been discussed as being configured to capture images of the patient's arm and the patient ends of the blood lines 102, 104, the image sensors 926, 928 may additionally or alternatively capture images of other objects in or near the blood treatment system 9 in order to determine tension along the blood lines 102, 104.

While the signals from the various above-described sensors 226, 228, 326, 328, 526, 528, 626, 628, 726, 826, 926 have been described as being transmitted to and processed by the blood treatment machine console 210 to determine tension along the blood lines 102, 104, the electronics and/or controls that receive and interpret output signals from the sensors 226, 228, 326, 328, 526, 528, 626, 628, 726, 826, 926 can be alternatively or additionally located in the treatment module 220, the arm 280, and/or elsewhere.

In some implementations, one or more of above-discussed sensors 226, 228, 326, 328, 526, 528, 626, 628, 726, 826, 926 are wireless sensors that communicate signals wirelessly to the blood treatment machine console 210, the treatment module 220, the arm 280, and/or elsewhere using any suitable form of wireless communication, including, but not limited to, WiFi, Bluetooth, near field communication, etc. In some implementations, one or more of above-discussed sensors 226, 228, 326, 328, 526, 528, 626, 628, 726, 826, 926 are wired to one of more of the blood treatment machine console 210, the treatment module 220, and the arm 280, and communicate signals over the wired connections to the blood treatment machine console 210, the treatment module 220, and/or the arm 280.

In some embodiments, there are additionally or alternatively sensors located in the arm 280 to determine the position, orientation, movement, and/or rate of movement of the treatment module 220. Such sensors can be angle sensors, path sensors, range sensors, accelerometers and/or other types of sensors, and can be used to improve the accuracy of positioning and moving the treatment module 220, as described above. For example, during repositioning of the treatment module 220 to prevent dislodgement of the blood lines 102, 104 or disconnection of the needles 134, 136, sensors located in the arm 280 can transmit signals to the blood treatment machine console 210 indicating the position, orientation, movement, and/or rate of movement of the module 220 in real-time during movement of the arm 280 to ensure accurate positioning of the treatment module 220.

While the arm 280 is depicted in FIGS. 1, 3-9 as being coupled to and extending from a front portion of the blood treatment machine console 210, the arm 280 can be coupled to other portions of the blood treatment machine console 210, such as a side of the blood treatment machine console 210 or the back of the blood treatment machine console 210. Similarly, while the arm 280 is depicted in FIGS. 1, 3-9 as being coupled to and extending from back of the treatment module 220, the arm 280 can be coupled to other portions of the treatment module 220, such as a side of the treatment module 220.

In addition, while the arm 280 is described as being capable of movement in three dimensions, the arm 280 may have an alternative design resulting in movement in a different number of dimensions. As such, the arm 280 may have a different number of degrees of freedom in its movement. For example, in some implementations, the arm 280 may be configured to be capable of movement along a single plane. For example, the arm 280 can be configured to extend outward from the blood treatment machine console 210 and retract inward towards the blood treatment machine console 210 in a single plane. In some implementations, in response to detecting strain along the blood lines 102, 104, the blood treatment machine console 210 automatically controls the arm coupled to the treatment module 220 to extend outward from the blood treatment machine console 210 along a single plane.

While the blood treatment systems discussed above have been described as including a dialyzer with an internal blood pump, the blood pump can alternatively or additionally be located external to the dialyzer. In some implementations, for example, the treatment module 220 includes a blood pump, such as a peristaltic pump, that interacts with the arterial line 102 for pumping blood through the dialyzer.

While the blood treatment systems discussed above have been described as machines that carry out hemodialysis and/or hemodiafiltration, the concepts described herein can be applied to any of various other types of blood treatment systems, including systems for carrying out hemofiltration, ultrafiltration, peritoneal dialysis, apheresis, and cardiopulmonary bypass procedures.

A number of embodiments have been described. Nevertheless, it will be understood that various modifications may be made without departing from the spirit and scope of the disclosure. Accordingly, other embodiments are within the scope of the following claims.

What is claimed is:
1. A blood treatment system comprising:
 a blood treatment machine comprising an arm;
 a dialyzer configured to be coupled to the blood treatment machine;
 a blood line having a first end configured to be connected to the dialyzer and a second end configured to be connected to a needle for insertion into a patient; and
 one or more sensors operable to transmit, to the blood treatment machine, data related to tension along the blood line,
 wherein the blood treatment machine is configured to control movement of the arm based on the data related to tension along the blood line.
2. The system of claim 1, wherein the blood treatment machine comprises:
 a treatment module including a structure for coupling with the dialyzer,
 a blood treatment machine console configured to control the treatment module; and
 the arm coupled to and extending between the treatment module and the blood treatment machine console, wherein the blood treatment machine console is configured to control movement of the arm to automatically reposition the treatment module based on the data related to tension along the blood line.
3. The system of claim 2, wherein the arm is configured to move the treatment module in a direction determined, based on the data related to tension along the blood line, to either prevent disconnection of the blood line from the dialyzer or prevent dislodgement of the needle from the patient when the needle is in the patient.

4. The system of claim 2, wherein the one or more sensors are configured to wirelessly transmit the data related to tension along the blood line to the blood treatment machine console.

5. The system of claim 2, wherein the arm includes one or more adjustable joints by which the arm can be articulated into multiple differing positions relative to the blood treatment machine console.

6. The system of claim 1 wherein the one or more sensors are configured to detect strain along the blood line.

7. The system of claim 6, wherein:
the one or more sensors are attached to a treatment module of the blood treatment machine, and
each of the one or more sensors is in contact with the blood line.

8. The system of claim 7, wherein at least one of the one or more sensors is positioned along the blood line proximate the second end of the blood line.

9. The system of claim 6, wherein the one or more sensors are embedded within the blood line.

10. The system of claim 6, wherein at least one of the one or more sensors is coupled to a joint of the arm of the blood treatment machine, and the arm extends from and is coupled to a treatment module of the blood treatment machine.

11. The system of claim 1, wherein the one or more sensors are configured to detect a position of a portion of the blood line.

12. The system of claim 11, wherein the one or more sensors comprise one or more accelerometers coupled to the blood line.

13. The system of claim 11, wherein the one or more sensors comprise one or more image sensors configured to detect the position of the portion of the blood line.

14. The system of claim 1, wherein:
the one or more sensors are configured to detect a position of the patient when the patient is connected to the blood line; and
the data related to tension along the blood line comprises data related to the position of the patient.

15. The system of claim 14, wherein the one or more sensors comprise an image sensors configured to detect light reflected by a reflective material.

16. The system of claim 15, further comprising a device comprising the reflective material, the device being configured to be positioned on an arm of the patient.

17. The system of claim 14, wherein the one or more sensors comprise one or more image sensors configured to track movement of an arm of the patient.

18. A blood treatment machine comprising:
a treatment module including a structure for coupling with a dialyzer,
a blood treatment machine console configured to control the treatment module; and
an arm coupled to and extending between the treatment module and the blood treatment machine console, wherein the blood treatment machine console is configured to control movement of the arm to automatically reposition the treatment module in response to data received from one or more sensors related to tension along a blood line coupled to the dialyzer.

19. The blood treatment machine of claim 18, wherein the arm includes one or more adjustable joints by which the arm can be articulated into multiple differing positions relative to the blood treatment machine console.

20. The blood treatment machine of claim 18, wherein the data received from one or more sensors comprises data related to tension along a blood line that is coupled to the dialyzer and coupled to a needle configured to be inserted in a patient.

21. The blood treatment machine of claim 20, wherein the arm is configured to move the treatment module in a direction determined, based on the data related to tension along the blood line, to prevent disconnection of the blood line from the dialyzer or to prevent dislodgement of the needle from the patient when the needle is in the patient.

22. The blood treatment machine of claim 20, wherein the data received from the one or more sensors comprises data related to strain along the blood line.

23. The blood treatment machine of claim 18, wherein the data received from the one or more sensors comprises data related to a position of a portion of the blood line coupled to the dialyzer.

24. The blood treatment machine of claim 23, wherein the data received from the one or more sensors comprises image data related to the position of the portion of the blood line.

25. The blood treatment machine of claim 18, wherein the data received from one or more sensors comprises data related to a position of a patient connected to the blood line coupled to the dialyzer.

26. The blood treatment machine of claim 25, wherein the data received from the one or more sensors comprises image data indicating light reflected by a reflective material.

27. The blood treatment machine of claim 25, wherein the data received from the one or more sensors comprises image data indicating a position of an arm of the patient.

* * * * *

UNITED STATES PATENT AND TRADEMARK OFFICE
CERTIFICATE OF CORRECTION

Page 1 of 1

PATENT NO.         : 11,338,072 B2
APPLICATION NO.    : 16/848410
DATED              : May 24, 2022
INVENTOR(S)        : Eric Bergman and Lynn E. Jensen It is certified that error appears in the above-identified patent and that said Letters Patent is hereby corrected as shown below:

In the Claims

Column 27, Line 41, in Claim 15, delete "an" and insert -- one or more --.

Signed and Sealed this
Twenty-fourth Day of January, 2023

Katherine Kelly Vidal
*Director of the United States Patent and Trademark Office*